United States Patent
Parks et al.

(10) Patent No.: US 11,684,637 B2
(45) Date of Patent: Jun. 27, 2023

(54) ONCOLYTIC VIRUSES FOR SENSITIZING TUMOR CELLS TO KILLING BY NATURAL KILLER CELLS

(71) Applicant: UNIVERSITY OF CENTRAL FLORIDA RESEARCH FOUNDATION, INC., Orlando, FL (US)

(72) Inventors: Griffith Parks, Orlando, FL (US); Alicja Copik, Casselberry, FL (US)

(73) Assignee: UNIVERSITY OF CENTRAL FLORIDA RESEARCH FOUNDATION, INC., Orlando, FL (US)

(*) Notice: Subject to any disclaimer, the term of this patent is extended or adjusted under 35 U.S.C. 154(b) by 693 days.

(21) Appl. No.: 16/616,671

(22) PCT Filed: May 25, 2018

(86) PCT No.: PCT/US2018/034655
§ 371 (c)(1),
(2) Date: Nov. 25, 2019

(87) PCT Pub. No.: WO2018/218151
PCT Pub. Date: Nov. 29, 2018

(65) Prior Publication Data
US 2021/0145876 A1 May 20, 2021

Related U.S. Application Data
(60) Provisional application No. 62/511,010, filed on May 25, 2017.

(51) Int. Cl.
| | | |
|---|---|---|
| A61K 35/76 | (2015.01) | |
| A61K 35/768 | (2015.01) | |
| C07K 14/705 | (2006.01) | |
| C12N 7/00 | (2006.01) | |
| A61K 35/17 | (2015.01) | |
| C07K 16/00 | (2006.01) | |

(52) U.S. Cl.
CPC ............ *A61K 35/17* (2013.01); *A61K 35/768* (2013.01); *C07K 14/705* (2013.01); *C07K 16/00* (2013.01); *C12N 7/00* (2013.01); *C12N 2760/18721* (2013.01); *C12N 2760/18732* (2013.01); *C12N 2760/18745* (2013.01)

(58) Field of Classification Search
None
See application file for complete search history.

(56) References Cited

U.S. PATENT DOCUMENTS

| | | | |
|---|---|---|---|
| 3,610,795 A | 10/1971 | Antoine | |
| 2002/0187543 A1* | 12/2002 | Curiel | C12N 15/86 |
| | | | 435/235.1 |
| 2009/0214590 A1* | 8/2009 | Sundick | A61K 39/145 |
| | | | 435/235.1 |
| 2010/0178684 A1 | 7/2010 | Woo et al. | |
| 2011/0086058 A1 | 4/2011 | Jiang et al. | |
| 2011/0318355 A1 | 12/2011 | Calatrava et al. | |
| 2014/0134162 A1 | 5/2014 | Stavenhagen et al. | |
| 2014/0271677 A1 | 9/2014 | Palese et al. | |
| 2015/0190471 A1* | 7/2015 | Copik | A61P 37/02 |
| | | | 435/375 |
| 2016/0362472 A1 | 12/2016 | Bitter et al. | |
| 2017/0007685 A1 | 1/2017 | Pasare et al. | |
| 2017/0056458 A1* | 3/2017 | Champion | C07K 14/56 |
| 2017/0067080 A1 | 3/2017 | He | |

FOREIGN PATENT DOCUMENTS

| | | |
|---|---|---|
| CA | 2670790 A1 | 6/2008 |
| WO | 2007048849 A1 | 5/2007 |
| WO | 2010072900 A1 | 7/2010 |
| WO | 2014037124 A1 | 3/2014 |
| WO | 2016046357 A1 | 3/2016 |
| WO | 2016069607 A1 | 5/2016 |
| WO | 2016109668 A1 | 7/2016 |
| WO | 2018083259 A1 | 5/2018 |

OTHER PUBLICATIONS

Blery et al. NKG2D-MICA Interaction: A Paradigm Shift in Innate Recognition. J Immunol 2018; 200:2229-2230.*
Ostrand-Rosenberg et al. The programmed death-1 immune-suppressive pathway: barrier to antitumor immunity. J Immunol. Oct. 15, 2014;193(8):3835-41.*
Extended European Search Report for Application No. 18806947 dated Feb. 26, 2021.
Choi K-J et al. "Concurrent delivery of GM-CSF and B7-1 using an oncolytic adenovirus elicits potent antitumor effect", Gene Therapy, Nature Publishing Group,London, GB, vol. 13, No. 13, Jul. 1, 2006, pp. 1010-1020.
Jiang et al. "The Control led Transgene Expression in Oncolytic Adenoviral Vectors with Major Late Promoter for Therapy of Cancer", Molecular Therapy, No longer published by Elsevier, vol. 13, Jan. 1, 2006,p. S251.
Kimberly M Clark et al. "Parainfluenza virus 5-based vaccine vectors expressing vaccinia virus (VACV) antigens provide long-term protection in mice from lethal intranasal VACV challenge", Virology, Elsevier, Amsterdam, NL, vol. 419, No. 2, Aug. 11, 2011, pp. 97-106.
Japanese Office Action issued for Application No. 2019-564782, dated Apr. 29, 2022.

(Continued)

*Primary Examiner* — Nianxiang Zou
(74) *Attorney, Agent, or Firm* — Meunier Carlin & Curfman LLC

(57) ABSTRACT

Disclosed are engineered oncolytic viruses, related fusion proteins and polynucleotides encoding them, and methods for treating cancer using the engineered viruses. In one aspect, disclosed herein are engineered oncolytic viruses, wherein the oncolytic virus expresses one or more exogenous membrane bound immune cell targeting ligands comprising an uncleaved signal anchor.

27 Claims, 11 Drawing Sheets

Specification includes a Sequence Listing.

(56) References Cited

OTHER PUBLICATIONS

Karlin, Samuel, and Stephen F. Altschul. "Methods for assessing the statistical significance of molecular sequence features by using general scoring schemes." Proceedings of the National Academy of Sciences 87.6 (1990): 2264-2268.
Karlin, Samuel, and Stephen F. Altschul. "Applications and statistics for multiple high-scoring segments in molecular sequences." Proceedings of the National Academy of Sciences 90.12 (1993): 5873-5877.
Altschul, Stephen F., et al. "Basic local alignment search tool." Journal of molecular biology 215.3 (1990): 403-410.
Altschul, Stephen F., et al. "Gapped BLAST and PSI-BLAST: a new generation of protein database search programs." Nucleic acids research 25.17 (1997): 3389-3402.
Creighton, Proteins: Structure and Molecular Properties, W. H. Freeman & Co., San Francisco pp. 88[1983].
Wansley, Elizabeth K., and Griffith D. Parks. "Naturally occurring substitutions in the P/V gene convert the noncytopathic paramyxovirus simian virus 5 into a virus that induces alpha/beta interferon synthesis and cell death." Journal of virology 76.20 (2002): 10109-10121.
Parks, Griffith D., and Robert A. Lamb. "Topology of eukaryotic type II membrane proteins: importance of N-terminal positively charged residues flanking the hydrophobic domain." Cell 64.4 (1991): 777-787.
Parks, Griffith D., and R. A. Lamb. "Role of NH2-terminal positively charged residues in establishing membrane protein topology." Journal of Biological Chemistry 268.25 (1993): 19101-19109.
Gainey, Maria D., Mary J. Manuse, and Griffith D. Parks. "A hyperfusogenic F protein enhances the oncolytic potency of a paramyxovirus simian virus 5 P/V mutant without compromising sensitivity to type I interferon." Journal of virology 82.19 (2008): 9369-9380.
Wansley, Elizabeth K., et al. "Growth sensitivity of a recombinant simian virus 5 P/V mutant to type I interferon differs between tumor cell lines and normal primary cells." Virology 335.1 (2005): 131-144.
Parks, Griffith D., et al. "Controlled cell killing by a recombinant nonsegmented negative-strand RNA virus." Virology 293.1 (2002): 192-203.
Hiebert, Scott W., and Robert A. Lamb. "Cell surface expression of glycosylated, nonglycosylated, and truncated forms of a cytoplasmic protein pyruvate kinase." The Journal of cell biology 107.3 (1988): 865-876.
Kundu, A. M. I. T. A. B. H. A., M. Abdul Jabbar, and Debi P. Nayak. "Cell surface transport, oligomerization, and endocytosis of chimeric type II glycoproteins: role of cytoplasmic and anchor domains." Molecular and cellular biology 11.5 (1991): 2675-2685.
Aref, Sarah, Katharine Bailey, and Adele Fielding. "Measles to the rescue: a review of oncolytic measles virus." Viruses 8.10 (2016): 294.
Matveeva, Olga V., et al. "Oncolysis by paramyxoviruses: preclinical and clinical studies." Molecular Therapy-Oncolytics 2 (2015): 15017.
Shobana, Raghunath, Siba K. Samal, and Subbiah Elankumaran. "Prostate-specific antigen-retargeted recombinant newcastle disease virus for prostate cancer virotherapy." Journal of virology 87.7 (2013): 3792-3800.
Hastie, Eric, and Valery Z. Grdzelishvili. "Vesicular stomatitis virus as a flexible platform for oncolytic virotherapy against cancer." The Journal of general virology 93.Pt 12 (2012): 2529.
Examination report No. 1 Australian Application No. 2018273963, dated Jul. 4, 2022.
Cheng, T. L. and Roffler, S., 'Membrane-Tethered Proteins for Basic Research, Imaging, and Therapy,' 2008, Medicinal Resaerch Reviews, vol. 28, No. 6, pp. 885-928 .doi: 10.1002/med.20127.
Bagshawe, et al., Br. J. Cancer, 58:700-703, (1988).
Bagshawe, K.D., Br. J. Cancer, 60:275-281, (1989).
Battelli, et al., Cancer Immunol. Immunother., 35:421-425, (1992).
Brown and Greene, DNA and Cell Biology 10:6, 399-409 (1991).
Ferrone et al., eds., Noges Publications, Park Ridge, N.J., (1985) Ch. 22 and pp. 303-357.
Gainey, et al., Journal of virology 82.19 (2008): 9369-9380.
Hughes et al., Cancer Research, 49:6214-6220, (1989).
Litzinger and Huang, Biochimica et Biophysica Acta, 1104:179-187, (1992).
Pietersz and McKenzie, Immunolog. Reviews, 129:57-80, (1992).
Roffler, et al., Biochem. Pharmacol, 42:2062-2065, (1991).
Senter, et al., Bioconjugate Chem., 2:447-451, (1991).
Senter, et al., Bioconjugate Chem., 4:3-9, (1993).
Smith et al., Antibodies in Human Diagnosis and Therapy, Haber et al., eds., Raven Press, New York (1977) pp. 365-389.
International Preliminary Report on Patentability issued for Application No. PCT/US2018/034655, dated Dec. 5, 2019.
International Search Report and Written Opinion for International Application No. PCT/US2018/034655 dated Oct. 2, 2018, 19 pages.
English translation of Chinese office action issued in CN 201880047292.0, dated Dec. 29, 2022.

\* cited by examiner

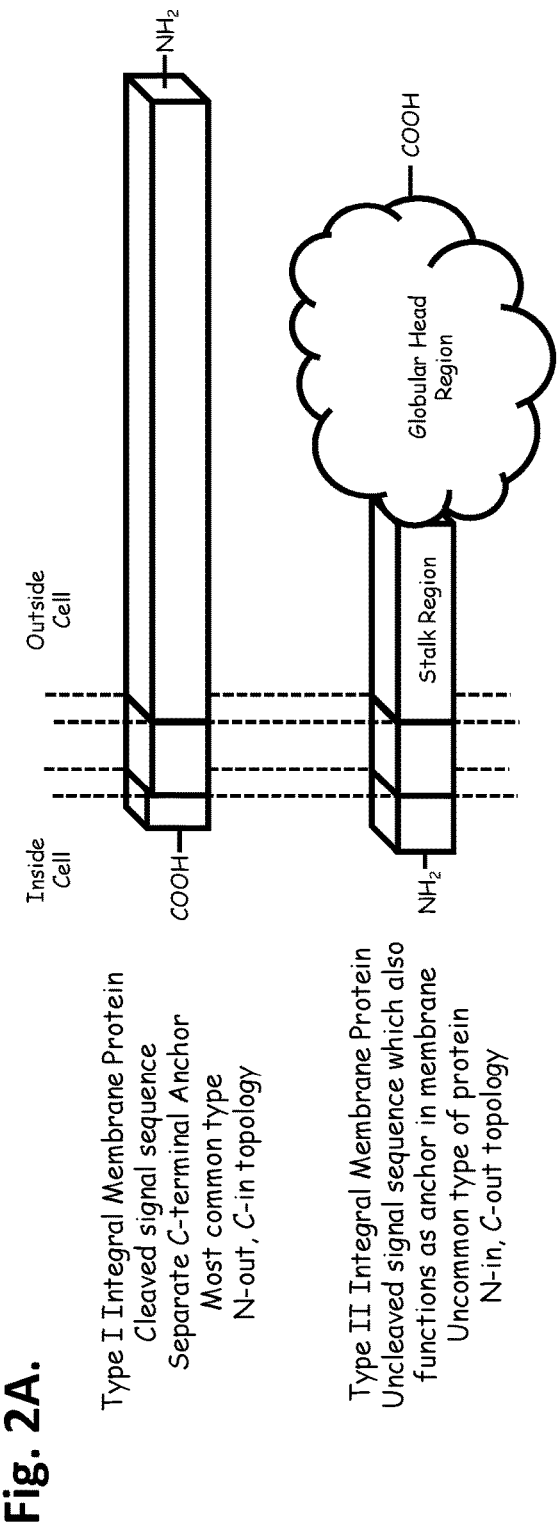
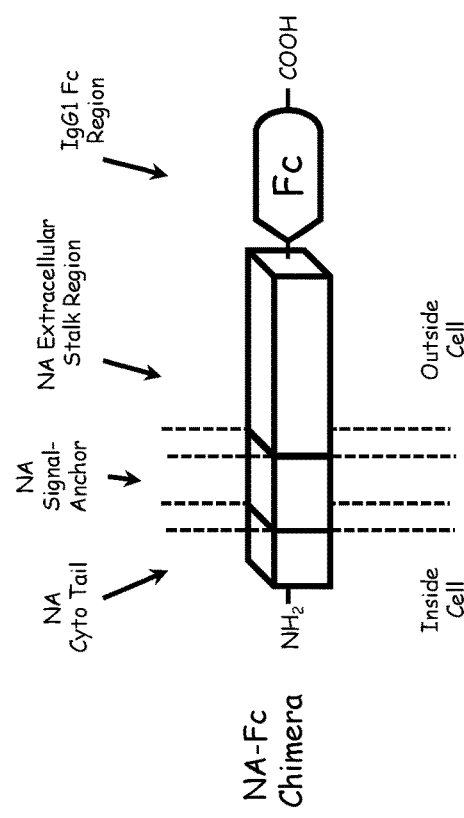
Fig. 2A.
Fig. 2B.

ONCOLYTIC VIRUSES FOR SENSITIZING TUMOR CELLS TO KILLING BY NATURAL KILLER CELLS

CROSS REFERENCE TO RELATED APPLICATIONS

This application is a national stage application filed under 35 U.S.C. § 371 of PCT/US2018/034655, filed May 25, 2018, which claims the benefit of U.S. Provisional Patent Application No. 62/511,010, filed on May 25, 2017, applications which are incorporated herein by reference in their entirety.

I. BACKGROUND

Oncolytic viruses (OVs) hold high promise as a cancer treatment. OVs selectively spread in cancer cells and cause a massive cytopathic effect. These virally infected, dying cancer cells further recruit immune cells such as NK cells or cytotoxic T cells to "clean up" infected cancer cells that escaped the viral killing. However, cancer patients frequently have compromised immune systems that fail at doing the job of killing and/or removing the infected target cancer cells. Accordingly, what are needed are new oncolytic viruses and methods of using said cells that can offer improved outcomes.

II. SUMMARY

Disclosed are methods and compositions related to engineered or modified oncolytic viruses.

In one aspect, disclosed herein are engineered oncolytic viruses wherein the oncolytic virus expresses one or more exogenous membrane bound immune cell targeting ligands comprising an uncleaved signal anchor.

Also disclosed herein are fusion proteins comprising an uncleaved signal anchor domain comprising: a cytoplasmic tail region, a transmembrane region and an extracellular stalk region; and an immune cell targeting ligand comprising an N-terminus fused to a C-terminus of the extracellular stalk region.

In one aspect, disclosed herein are oncolytic viruses and/or fusion peptides, polypeptides, or proteins of any preceding aspect; wherein the one or more exogenous membrane bound immune cell targeting ligands comprises an engineered immunoglobulin Fc domain, a protein agonist of the NK cell receptor NKG2D (such as, for example RAET1, RAET1E, RAET1G, RAET1H, RAET1L, RAET1N, MICA, MICB), a protein epitope that is reactive to anti-CD19 (such as CD19), and/or a protein epitope that is reactive to anti-CD20 (such as CD20).

Also disclosed are oncolytic viruses and/or fusion peptides, polypeptides, or proteins of any preceding aspect; wherein the exogenous membrane bound immune cell targeting ligand is an immunoglobulin Fc domain and the immunoglobulin Fc domain (such as, an IgG1, IgG2, IgG3, or IgG4 Fc domain) is modified to have an inverted orientation with the amino terminal end facing intracellularly (i.e., the Fc is expressed on the extracellular side of the cell surface with its N-terminal side being attached to a membrane anchor peptide near the surface of cell membrane rather than the N-terminal side being at maximal distance from the cell surface). In one aspect, disclosed herein are oncolytic viruses and/or fusion peptides, polypeptides, or proteins of any preceding aspect; wherein the N-terminus of the Fc domain is fused to the C-terminus of the extracellular stalk region of the uncleaved signal anchor.

In one aspect, disclosed herein are engineered oncolytic viruses, wherein the engineered oncolytic virus is a fusogenic oncolytic virus. In some aspect, the fusogenic oncolytic virus can be modified or engineered parainfluenza virus type 5. Also disclosed are fusogenic oncolytic viruses of any preceding aspect, wherein the fusogenic oncolytic virus comprises a gene which codes for a peptide that allows a hyperfusogenic property that allows tumor cells to fuse. In one aspect, the oncolytic virus is modified or engineered to comprise the fusion peptide, polypeptide, or protein of any preceding aspect.

Also disclosed are oncolytic viruses of any preceding aspect, wherein the oncolytic virus is engineered to express one or more of IL-2, IL-12, IL-18, IL-21 or IL-15.

In one aspect, disclosed herein are methods of treating cancer, comprising administering to a subject an engineered oncolytic virus and/or fusion peptides, polypeptides, or proteins of any preceding aspect.

Also disclosed are method of treating cancer of any preceding aspect, wherein the method further comprises adoptively transferring antibodies or immune cells (for example, NK cells, genetically modified NK cell, and/or CAR T cells).

In one aspect, disclosed herein are methods of treating cancer of any preceding aspect, wherein the NK cells are stimulated and expanded with one or more NK cell stimulating agents, such as, for example, a cytokine, growth factor, synthetic ligand, NK cell stimulating particle, NK cell stimulating exosome, or NK cell stimulating feeder cell.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows a schematic of tumors lacking targetable antigen are treated and infected with tumor targeting oncolytic virus engineered to deliver membrane bound Fc region of antibody (MB Fc) or a membrane bound-targetable ligand (MB_TL); (e.g. RAET1, RAET1E, RAET1G, RAET1H, RAET1L, RAET1N, MICA, MICB, CD19, and/or CD20). If a MB_TL that is not a NK cell receptor agonist is used, tumors can be treated with therapeutic antibody against TL (e.g. anti-CD20-rituximab, ofatumumab, obtinutuzumab, veltuzumab, or ocrelizumab or anti-CD19 MDX1342, MEDI-551, AFM11, XmAb 5871, MOR-208, SGN-19A, SAR3419, Blinatumomab, or taplitumomab). Tumors marked with Fc or anti-TL antibody can then treated with adoptively transferred cells capable of antibody dependent cell cytotoxicity (ADCC) such as for example CD16+ NK cells.

FIGS. 2A and 2B show the construction of a membrane bound immune cell targeting ligand comprising an uncleaved signal anchor. FIG. 2A shows the structure of Type I and Type II integral membrane proteins and the signal anchors for each. FIG. 2B shows the structure of the uncleaved signal anchor used in the membrane bound immune cell targeting ligand.

Figure 6:
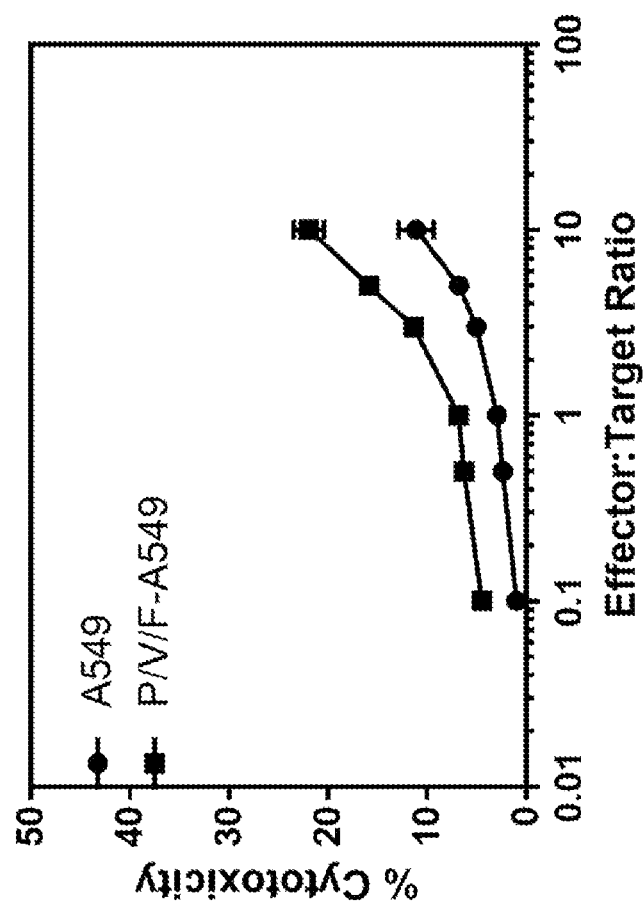

FIG. 6 shows P/V/F virus sensitize A549 cells to NK cell killing. A549 lung cancer cell line was mock infected or infected with P/V/F virus. Following infection NK cells were added to the cells at indicated ratios and incubated for 4 hours. Cell death was measured using Cytotox Glow Assay. NK only and target (mock or P/V/F infected) only wells were included as controls.

Figure 7:
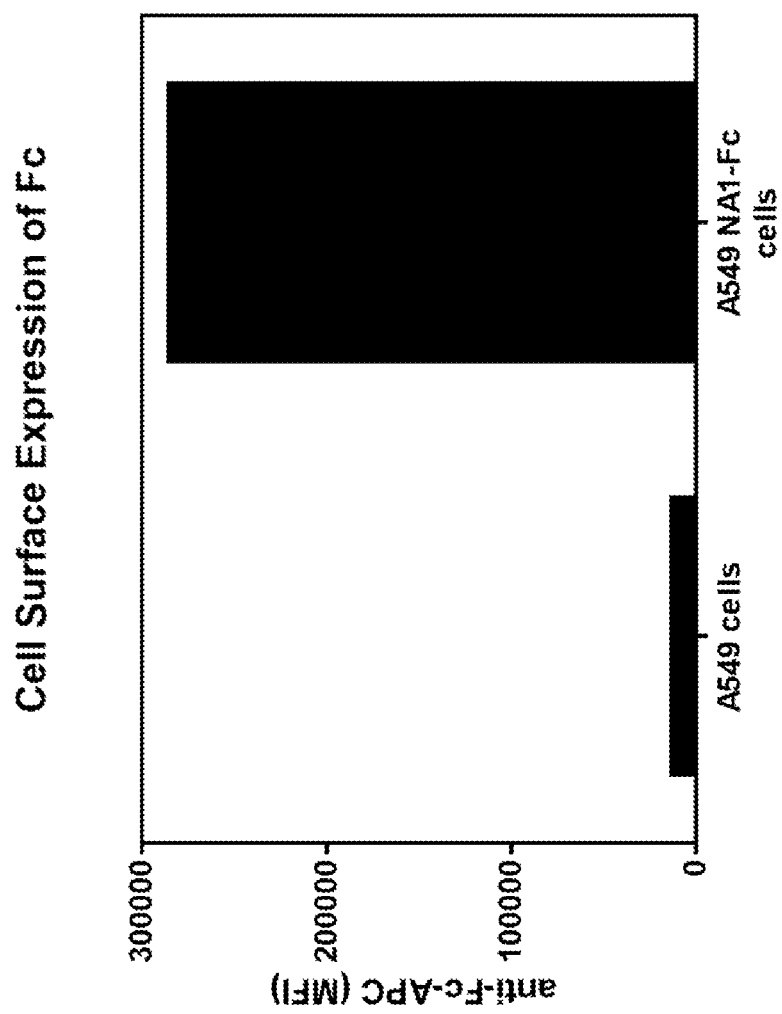

FIG. 7 shows A549 lung cancer cells transfected with NA1-Fc construct under Zeocin selection express Fc on the cells surface. A549 lung cancer cell line was transfected with construct encoding expression of NA1-Fc and cultured in presence of Zeocine. Cell were stained with anti-humanFc-APC antibody and analysed by flow cytometry. Parental cells were used as a control.

Figure 8:
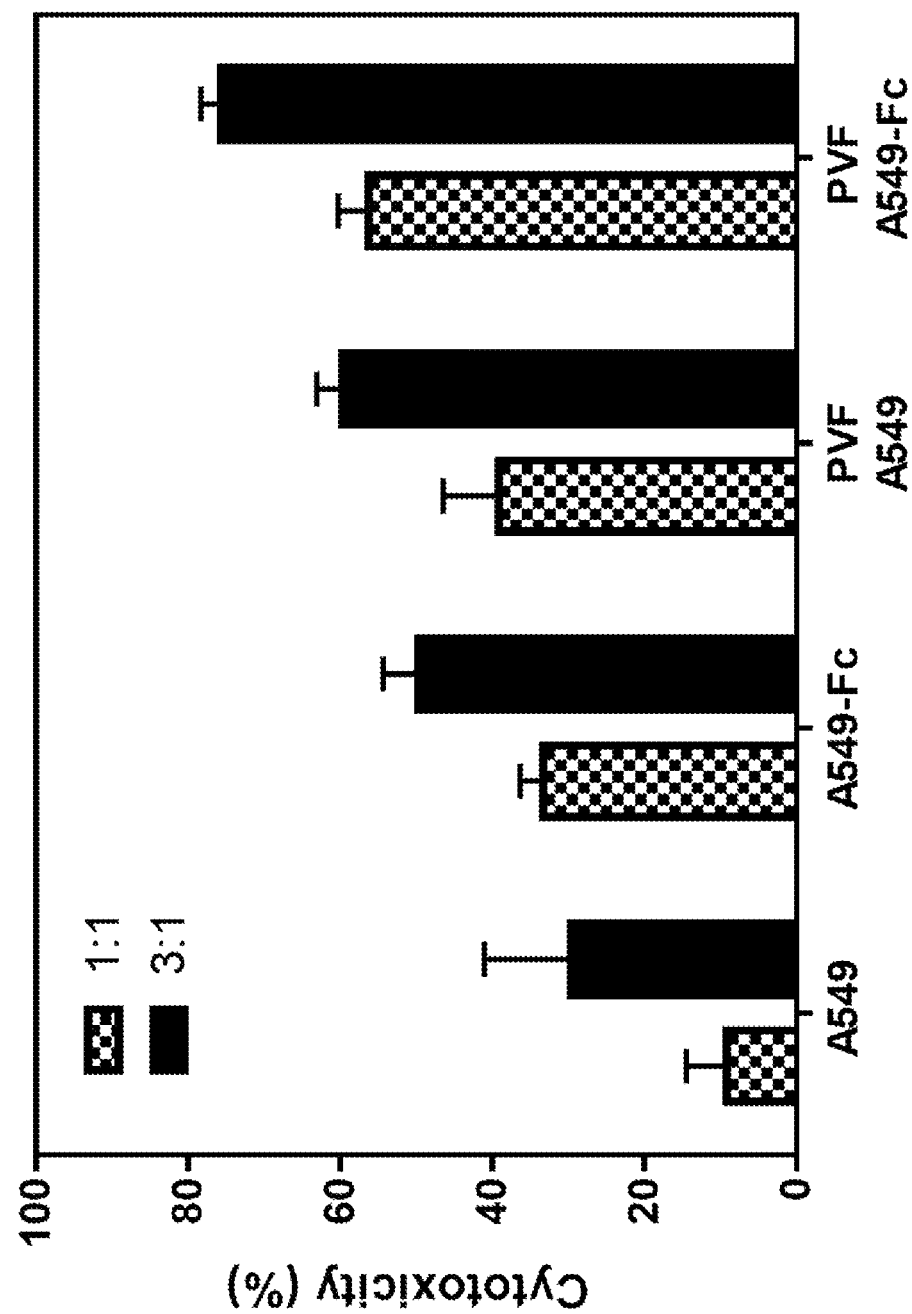

FIG. 8 shows the expression of Fc on tumors as well as infection with P/V/F increase killing of A549 cells by NK cells. A549 cells or A549 cells stably expressing Fc on the surface (A549-Fc) were infected with mock or P/V/F and incubated with NK cells at 1:1 or 1:3 target to NK cell ratio. Cell death was determined by flow cytometry measuring live cell events in the target gate with reference to controls containing respective target only cells.

Figure 9:
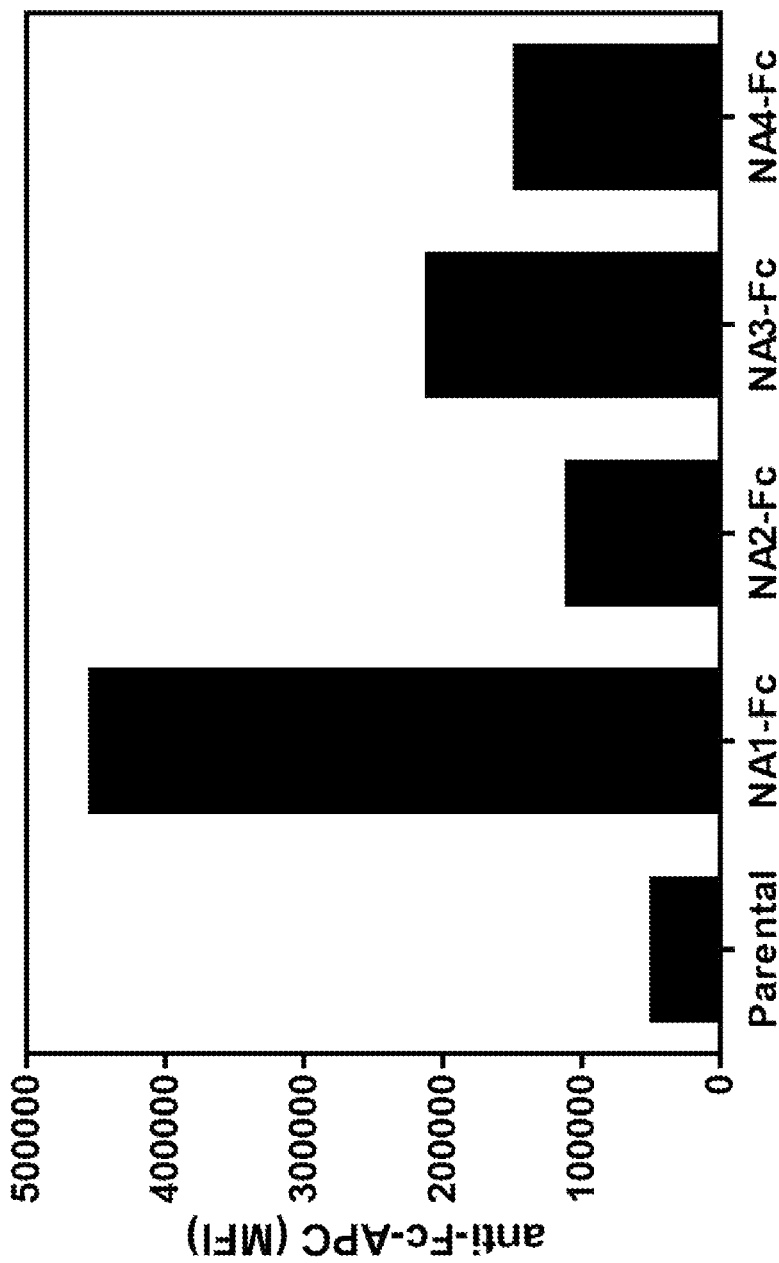

FIG. 9 shows that SKOV-3 ovarian cancer cells transfected with NA1-Fc-NA4-Fc constructs express Fc on the cells surface after FACS sorting. SKOV-3 ovarian cancer cell line was transfected with constructs encoding expression of NA1-Fc, NA2-Fc, NA3-Fc or NA4-Fc. After few days cells were stained with anti-human Fc-APC antibody and sorted by FACS to enrich for Fc-expressing cell population cytometry. Sorted cells have stable but variable level of expression of Fc for all constructs tested. Parental cells were used as a control.

Figure 10:
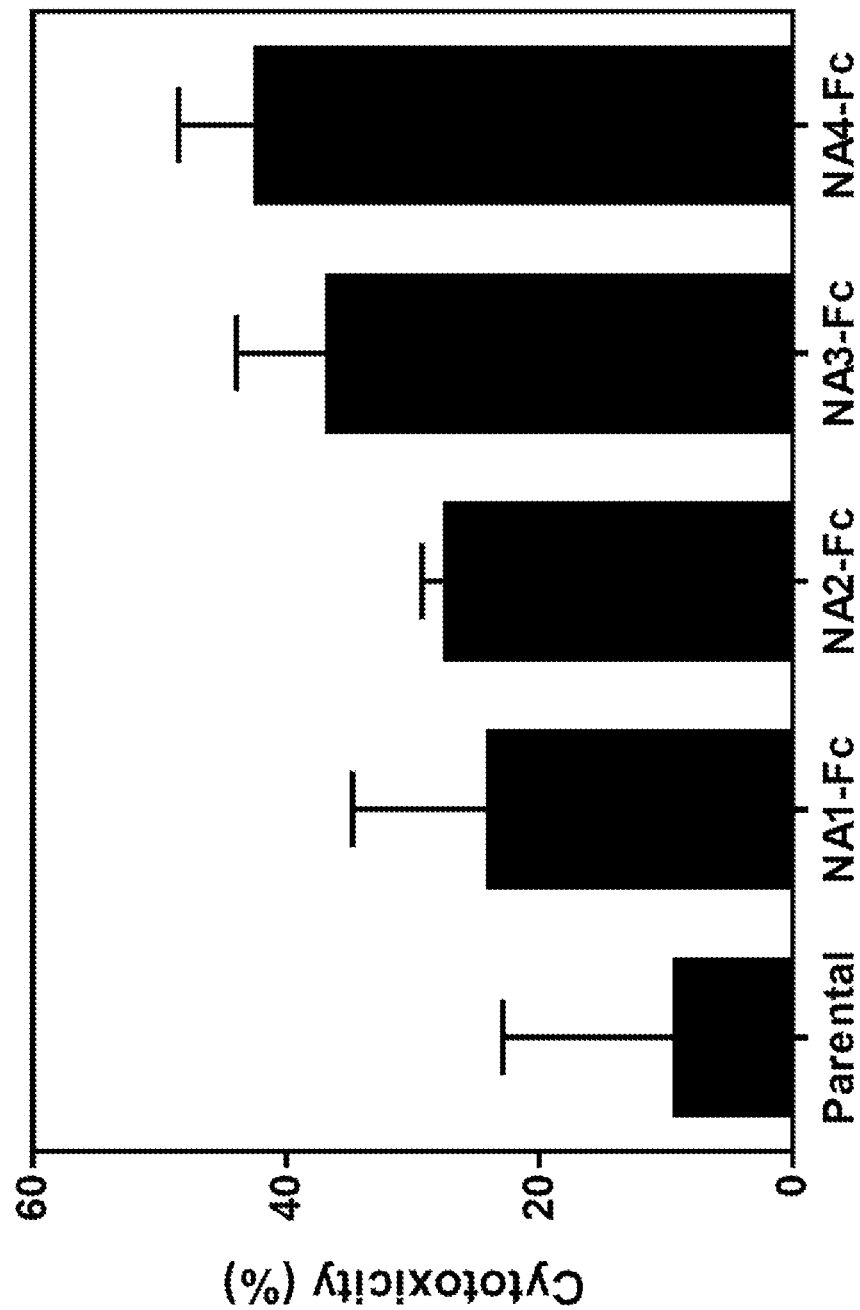

FIG. 10 shows that the increased length of the NA stalk improves NK cell killing via recognition of the surface expressed Fc domain. SKOV-3 cells with or without stable expression of (NA1-NA4)-Fc were mixed with NK cells at a 3:1 ratio of NK:Targets. Cell death was determined by flow cytometry measuring live cell events in the target gate with reference to controls containing respective target only cells. Killing correlates with the length of the NA stalk rather then the density of the Fc on the cells surface of SKOV-3 (FIG. 9).

Figure 11:
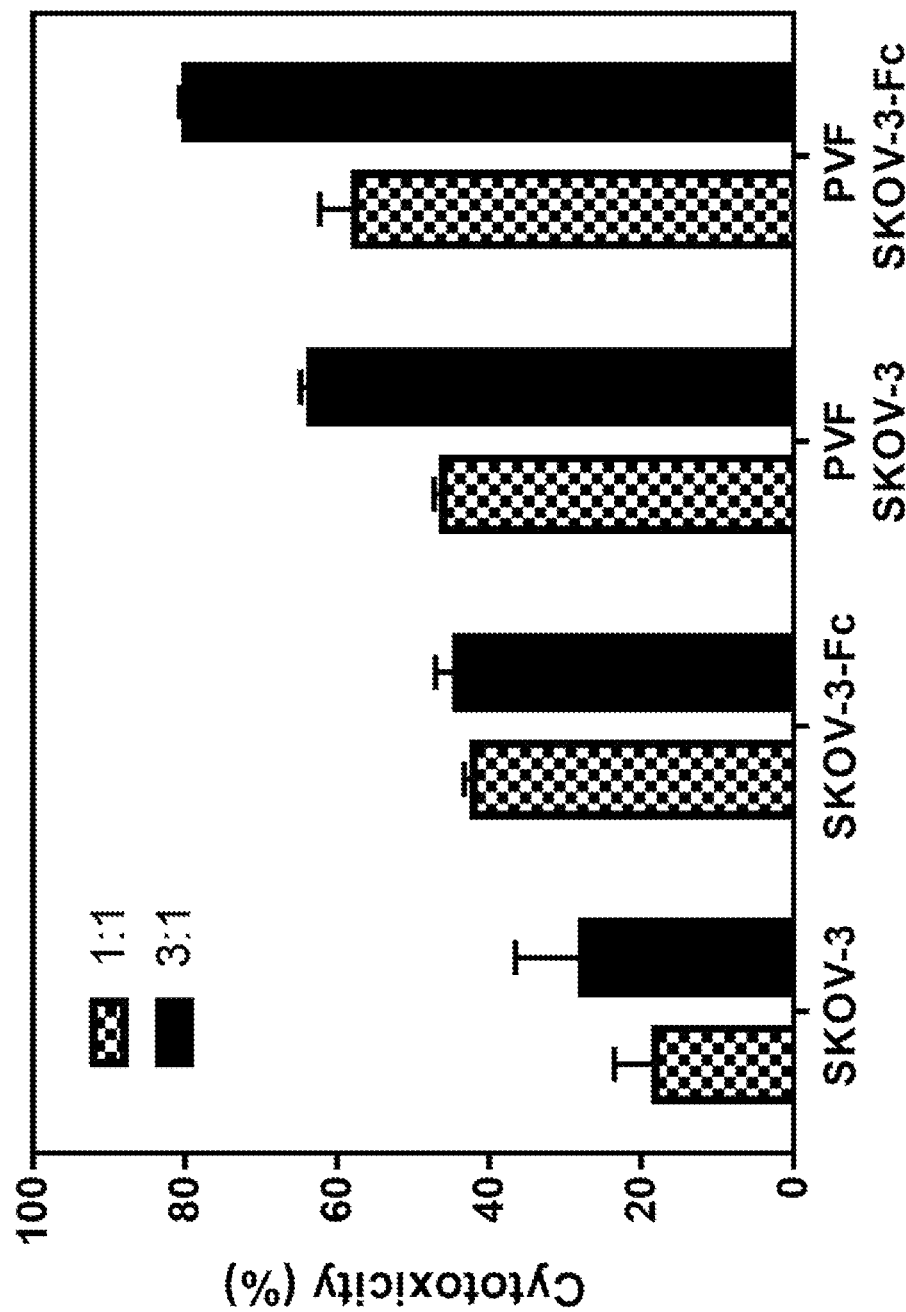

FIG. 11 shows that the expression of Fc on tumors as well as infection with P/V/F increase killing of SKOV-3 cells by NK cells. SKOV-3 cells or SKOV-3 cells stably expressing NA1-Fc on the surface (SKOV-3-Fc) were infected with mock or P/V/F and incubated with NK cells at 1:1 or 1:3 target to NK cell ratio. Cell death was determined by flow cytometry measuring live cell events in the target gate with reference to controls containing respective target only cells. Both, expression of Fc on the surface as well as infection with P/V/F leads to increased killing of SKOV-3 cells by NK cells and this effect is additive.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

As used herein, "N-terminal side" or "amino terminal end" refers to directionality of a peptide, polypeptide, or protein and may not mean the N-terminus. In some aspects, where a chimeric or fusion peptide, polypeptide, or protein is discussed, the N-terminal side may refer only to a component of the chimeric or fusion peptide, polypeptide, or protein and not the entire structure. For example, where a Fc domain comprising an uncleaved signal anchor is discussed, and the Fc domain is described as having an inverted orientation with the amino terminal end or N-terminal side facing intracellularly, contemplated herein are chimeric or fusion peptide, polypeptide, or protein wherein the signal anchor is at the N-terminus of the chimeric or fusion construct and actually spans the cellular membrane. Thus, in such a chimera, the anchor is closer to the amino terminus than the Fc domain, but the directionality of the Fc domain has the N-terminal side facing the cell which is inverted relative to the orientation of the Fc domain in a typical B cell which would typically have the carboxy end spanning the cellular membrane and amino terminal end extending to the extracellular matrix.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular oncolytic virus or fusion protein is disclosed and discussed and a number of modifications that can be made to a number of molecules including the oncolytic virus and/or fusion protein are discussed, specifically contemplated is each and every combination and permutation of oncolytic virus and/or fusion protein and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Oncolytic viruses (OVs) which preferentially infect and kill cancer cells hold high promise as a cancer treatment. OVs selectively spread in cancer cells and cause a massive cytopathic effect. These virally infected, dying cancer cells further recruit immune cells such as NK cells or cytotoxic T cells to "clean up" infected cancer cells that escaped the viral killing. Since, in cancer patients, the immune system is frequently compromised and fails at doing the job, combination with adoptive immune cell transfer can offer improved outcomes.

Immune cells such as NK cells, directly target the destruction of infected cells. NK cells, for example, efficiently destroy tumor cells, stressed cells, and virally infected cells by a variety of different methods. The first is by directly engaging target cells, permeating their membranes, and then injecting a protein that cleaves and activates several apoptotic proteins, thereby initiating programmed cell death (apoptosis) of the targeted cell. The surface of an NK cell also contains protein ligands that can bind and activate receptors, such as the receptor for tumor-necrosis factor (TNF)-related apoptosis-inducing ligand (TRAIL), on target cells that turn on internal signals for apoptotic programmed cell death. When stimulated, NK cells can also secrete cytokines such as INFγ and TNFα that not only inhibit viruses and tumors, but also signal invasion to other immune cells.

Through the use of recombinant nucleic acid modification, it is understood and herein contemplated that oncolytic viruses and/or fusion peptides, polypeptides, and proteins can be engineered to or otherwise modified so that expression of the fusion peptides, polypeptides or proteins in a cancer cell improves the NK cell recruitment to target cancer cells. As used interchangeably herein, the terms "fusion peptide(s)", "fusion polypeptide(s)", and "fusion proteins" refer to any peptide, polypeptide, or protein that has been engineered to comprise domains from two or more unrelated peptides, polypeptides, or proteins. In some aspects, the fusion peptide, polypeptides, or proteins comprise all or a portion of each of the component two or more peptide, polypeptide, or proteins that are joined to form the fusion.

Thus, one aspect of the invention pertains to engineered fusion proteins, i.e., exogenous membrane bound targeting ligands expressed by the engineered oncolytic viruses, as disclosed herein. As used herein, the term "fusion protein" is synonymous with "chimeric protein," and refers to a first, uncleaved signal anchor polypeptide comprising a cytoplasmic tail region, a transmembrane region and an extracellular stalk region as explained in further detail below, the first polypeptide operatively linked to an immune cell targeting ligand polypeptide. The term "operatively linked" refers to the fusion of the two polypeptides, i.e., fusion in-frame of each region to the other. Fusion may be accomplished with or without the use of a short polypeptide linker consisting of 2, 3, 4, 5, 6, 7, 8, 9, 20, 11, 12, 13, 14, 15, 16, 17, 18, 19 or 20 or more amino acids. For example, the targeting ligand polypeptide may be fused at its N-terminus to the C-terminus of the first polypeptide.

In one aspect, the fusion peptides, polypeptides, or proteins are exogenous membrane bound targeting ligands as disclosed herein. The fusion peptides, polypeptides or proteins thus can comprise an uncleaved signal anchor domain comprising: a cytoplasmic tail region, a transmembrane region and an extracellular stalk region; and an immune cell targeting ligand wherein the N-terminus of the immune cell targeting ligand is fused to a C-terminus of the extracellular stalk region. (See, e.g., FIG. 2B). In other words, when the fusion protein is expressed in a cell, the immune cell targeting ligand is bound to the cell membrane in an inverted orientation with respect to the cell, as compared to the naturally occurring orientation of the immune cell targeting ligand.

In one aspect, the uncleaved signal anchor domain is derived from a Type II integral membrane protein which is schematically depicted in the lower panel of FIG. 2A. A Type II integral membrane protein generally comprises an N-terminus inside the cell, i.e., a cytoplasmic tail region, a transmembrane region, an extracellular stalk region and a globular head region with the C-terminus. As disclosed herein, the uncleaved signal anchor domain comprises the cytoplasmic tail region, the transmembrane region, and the extracellular stalk region, but lacks the globular head region. The uncleaved signal anchor domain can comprise for example the relevant portions of a Type II integral membrane protein such as neuraminidase, parainfluenza virus hemagglutinin-neuraminidase, transferrin receptor, MHC class II invariant chain, P glycoprotein, asialoglycoprotein receptor, or a neutral endopeptidase. In an exemplary aspect, the uncleaved signal anchor domain comprises a neuraminidase signal anchor domain, as shown in FIG. 2B.

The immune cell targeting ligand is for example a ligand capable of binding, for example selectively binding an immune cell, and comprising an amino acid modification wherein the N-terminus of the ligand fuses or is fused to (via a peptide linker) to the C-terminus of the extracellular stalk domain of the uncleaved signal anchor domain. Ligands can be selected from known ligands that are capable of binding an immune cell such an NK cell, a B cell, a T cell and/or a CAR-T cell. Such ligands include, for example, an immunoglobulin Fc domain such as IgG1 (as shown in FIG. 2B), or alternatively IgG2, IgG3, or IgG4. Amino acid modifications to the Fc domain that are suitable for achieving the inverted orientation described herein include: 256A/K290A/S298A/E333A/K334A or L235V/F243L/R292P/Y300L/P396L. Alternatively, the targeting ligand is selected from an NK2GD ligand such as, for example, RAET1, RAET1E, RAET1G, RAET1H, RAET1L, RAET1N, MICA, and MICB; or an anti-ligand domain such as CD19 or CD20.

By way of non-limiting example, fusion proteins as disclosed herein encompass polypeptides comprising amino acid sequences sufficiently identical to or derived from the amino acid sequence of SEQ ID NO:1. Fusion proteins as disclosed herein encompass polypeptides having fewer or more amino acids than the full length sequence of SEQ ID NO:1, and exhibit the same membrane anchoring function with a targeting ligand as demonstrated by the fusion protein having the sequence of SEQ ID NO: 1. Examples of useful fusion proteins according to the present disclosure include a protein which comprises an amino acid sequence that has at least about 45%, preferably 55%, 65%, 75%, 85%, 95%, or 99% sequence identity with the amino acid sequence of SEQ ID NO: 1, and retains the functional activity of the fusion protein of SEQ ID NO:1. More specifically, a fusion protein according to the present disclosure can comprise an amino acid sequence having at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence identity to the amino acid sequence of SEQ ID NO: 1.

The percent identity of two amino acid sequences or of two nucleic acid sequences can be determined by aligning the two sequences end to end to optimize the number of amino acid or nucleotide matches between the two sequences, wherein for example gaps can be introduced in the sequence of a first amino acid or nucleic acid sequence to obtain the optimal alignment with a second amino or nucleic acid sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent sequence identity between the two sequences is a function of the number of identical positions shared by the sequences (i.e., % sequence identity is the number of identical positions/total number of positions×100).

The determination of percent sequence identity between two sequences may be accomplished using a mathematical algorithm. A non-limiting example of a mathematical algorithm as known in the art and utilized for the comparison of two sequences is the algorithm of Karlin and Altschul (1990) Proc. Nat'l Acad. Sci. USA 87:2264-2268, modified as in Karlin and Altschul (1993) Proc. Nat'l Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, word-length=12 to obtain nucleotide sequences similar or homologous to Adhesin nucleic acid molecules of the invention. To obtain gapped alignments for comparison purposes, Gapped BLAST can be utilized as described in Altschul et al. (1997) Nucleic Acids Res. 25:3389-3402. When utilizing BLAST and Gapped BLAST programs, the default parameters of the respective programs (e.g., XBLAST and NBLAST) can be used.

The fusion proteins and polynucleotides encoding them can be produced by standard recombinant DNA techniques as known in the art. For example, DNA fragments coding for the different polypeptide sequences are ligated together in-frame applying conventional techniques. Suitable techniques include by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, a fusion gene may be synthesized by conventional techniques including automated DNA synthesizers. Alternatively, PCR amplification of gene fragments may be carried out using anchor primers that give rise to complementary overhangs between two consecutive gene fragments, which can subsequently be annealed and reamplified to generate a chimeric gene sequence. (See, e.g., Current Protocols in Molecular Biology, Ausubel et al. eds., John Wiley & Sons: 1992).

A fusion gene encoding a fusion protein as disclosed herein can be created by removing the stop codon from a cDNA sequence encoding the first polypeptide, then adding a cDNA encoding the second polypeptide protein in frame through ligation or overlap extension PCR. Optionally, a short sequence of amino acids (for example, a sequence of about 2 to about 20 amino acids) can be engineered in as a linker between the first polypeptide and the second polypeptide. The resulting fusion gene which comprises a polynucleotide sequence encoding a fusion protein can then be introduced to the genome of a host virus, including for example an engineered oncolytic virus as disclosed herein. When the host virus contacts a host cell and delivers its modified genetic package to the cytoplasm of the cell, the fusion gene will then be expressed by the host cell as a single fusion protein.

As noted above, the disclosed oncolytic viruses can be modified or engineered to maximize the number of immune cells (for example NK cells, T cells, CART cells, Innate lymphoid cells, Macrophages, and B cells (including plasma cells)) at the target cancer site and thus increase the immune cell activity (for example, NK cell activity, T cell activity, CAR T cell activity, and/or B cell activity (including plasma cell and antibody activity) in eliminating cancer beyond that which an unmodified oncolytic virus would do. As used herein, "oncolytic viruses" refers to a virus that is tropic for and kills cancer cells. Oncolytic viruses can be engineered to selectively attack cancer cells. Accordingly, in one aspect, disclosed herein are engineered oncolytic viruses wherein the oncolytic viruses express one or more membrane bound immune cell targeting ligands comprising an uncleaved signal anchor. In some aspect, the engineered oncolytic viruses expresses one or more of the fusion peptides, polypeptides, or proteins disclosed herein.

In one aspect, the disclosed oncolytic viruses and/or fusion peptides, polypeptides, or proteins are modified to express or comprise one or more exogenous membrane bound immune cell targeting ligands (such as, for example, NK cell targeting ligands) for increasing the affinity towards NK cells. As used herein, exogenous membrane bound immune cell targeting ligands refers to any exogenous peptide, polypeptide, or protein that can serve as a target for immune cell activity including, but not limited to NK cell activity, B cell activity, T cell activity, and CAR T cell activity. Thus, in aspect, the oncolytic virus can comprise one or more peptides, polypeptides, or proteins comprising exogenous membrane bound immune cell targeting ligands including fusion proteins that comprise an exogenous membrane bound immune cell targeting ligand. The membrane bound immune cell targeting ligands of the disclosed oncolytic viruses and/or fusion peptides, polypeptides, or proteins can be bound by NK cells, B-cells, T-cells, or CAR T-cells. In one aspect, immune cell targeting ligands are membrane bound via modification to include a signaling anchor. Immune cell targeting ligands can, for example, comprise immunoglobulin Fc domains which are ligands for CD16 on NK cells, ligands for NKG2D receptors on NK cells, or targets for antibodies or CAR T cells. In one aspect, it is understood and herein contemplated that the exogenous membrane bound immune cell targeting ligands can be either bound directly by NK cell receptors such as, for example, Fc domains (for example IgG1, IgG2, IgG3, and/or IgG4), NK2GD ligands (for example, RAET1, RAET1E, RAET1G, RAET1H, RAET1L, RAET1N, MICA, and/or MICB), or can be bound indirectly by NK cells via the use of an anti-ligand antibody (for example CD19 or CD20 which can be bound by anti-CD19 or anti-CD20 antibodies) or can be directly targeted by anti-ligand CAR T cells (such as, for example, anti-CD19 CART cells). Accordingly, in one aspect, disclosed herein are fusion proteins comprising immune cell targeting ligands and oncolytic viruses comprising one or more immune cell targeting ligands, wherein the immune cell targeting ligand is an Fc domain selected from the group consisting of IgG1, IgG2, IgG3, and/or IgG4.

The Fc domain is the ligand to which CD16 (FcγRIII) which is found on the surface of NK cells binds. CD16 is one of the primary receptors on NK cells and when CD16 binds to the Fc portion of an antibody (for example, an IgG1, IgG2, IgG3, and/or IgG4 Fc domain), this activates the NK cells antibody-dependent cell mediated cytotoxicity (ADCC). However, the Fc portion of the antibody is typically only available when secreted. When the membrane bound antibody receptor found on B cells is present, the Fc portion is typically oriented to the cytosol of the cell. Accordingly, in the modified oncolytic viruses disclosed herein, the Fc domain is modified to have an inverted orientation with the amino terminal end faced intracellularly when expressed on membranes of infected tumor targets thus mimicking the orientation of an extracellular antibody bound to the surface of a cell. In one aspect, disclosed herein are modified or engineered oncolytic viruses expressing one or more exogenous membrane bound immune cell targeting ligands comprising an uncleaved signal anchor; wherein the one or more exogenous membrane bound immune cell targeting ligand is an immunoglobulin Fc domain (for example, an IgG1, IgG2, IgG3, and/or IgG4 Fc domain) modified to have an inverted orientation with the amino terminal end faced intracellularly (i.e., the Fc is expressed on the extracellular side of the cell surface with its N-terminal side being attached to a membrane anchor peptide near the surface of cell membrane rather than the N-terminal side being at maximal distance from the cell surface).

It is understood and herein contemplated that the Fc domain can be presented as a monomeric, dimeric, or multimeric construct. In one aspect, the Fc domain can be further modified to enhance antibody mediated killing, NK cell recognition, and control expansion of activating Fcγ receptors. For example, the Fc domain can be modified to increase affinity for CD16. Thus, for example, the Fc domain may comprise one or more mutations such as, for example, T256A, K290A, S298A, E333A, K334A, L235V, F243L, R292P, Y300L, and/or P396L. Similarly, the Fc domain can be further modified to increase selectivity of binding to the activating (IIa) vs, inhibitory Fc(IIb) receptor. Thus, for example, the Fc domain may comprise one or more mutations such as, for example, S239D, I332E, A330L, F243L, R292P, V305I, and/or P396L.

NKG2D is activating receptor on NK cells that triggers actin reorganization (cell polarization) and degranulation in target cells. NKG2D recognizes induced-self proteins which are typically completely absent or present only at low levels on surface of normal cells, but are overexpressed by infected, transformed, senescent and stressed cells. The ligands for NKG2D are from MHC class I polypeptide-related sequence (MIC) and retenoic acid early transcript 1 (RAET1)/ULBP families which appear on the surface of stressed, malignant transformed, and infected cells. MIC is a surface glycoprotein. The MIC family of proteins (MICA and MICB) are structurally similar to MHC, but do not associate with β2-microglobulin or peptides like MHC. MIC family proteins are comprised of an extracellular domain (an α1α2α3 domain), a transmembrane domain, and a C-terminal cytoplasmic tail. The RAET1 family are surface glycoproteins comprising an extracellular domain (an α1α2 domain), a transmembrane domain, and a C-terminal cytoplasmic tail. The RAET1 family serve as stressed induced ligands for NKG2D and are related to MHC class 1 molecules. In one aspect, disclosed herein are engineered oncolytic viruses and/or fusion peptides, polypeptides, or proteins comprising one or more exogenous membrane bound immune cell targeting ligand comprising an uncleaved signal anchor; wherein the one or more exogenous membrane bound immune cell targeting ligand is an NKG2D ligand (for example, RAET1, RAET1E, RAET1G, RAET1H, RAET1L, RAET1N, MICA, and/or MICB).

The exogenous membrane bound immune cell targeting ligands, i.e., the fusion proteins that are encoded by the engineered oncolytic viruses as disclosed herein are modified to present on the surface of the infected cancer cell. In one aspect, this membrane bound presentation can be achieved through the use of an uncleaved signal anchor. Signal anchors can comprise any signaling sequence that retains the encoded peptide, polypeptide, or protein on a cell surface membrane. For example, the signal anchor can be the transmembrane domain of neuraminidase, the signal-anchor from parainfluenza virus hemagglutinin-neuraminidase, the signal-anchor from the transferrin receptor, the signal-anchor from the MHC class II invariant chain, the signal-anchor from P glycoprotein, the signal-anchor from asialoglycoprotein receptor, or the signal-anchor from a neutral endopeptidase. Alternatively, the exogenous membrane bound immune cell targeting ligands can be modified to encode amino acid substitutions comprising additional positively charged amino acids on the amino terminal end. In one aspect, the exogenous membrane bound immune cell targeting ligand can be a fusion protein wherein the signal anchor is joined or fused to the targeting ligand through use of a linker such as a RS linker. Accordingly, in one aspect, are oncolytic viruses and/or fusion peptides, polypeptides, or proteins comprising one or more exogenous membrane bound immune cell targeting ligands, wherein the membrane bound immune cell targeting ligands comprises an uncleaved signal anchor. In one aspect, the immune cell targeting ligand comprises an immunoglobulin Fc domain comprising an amino acid modification wherein the N-terminus of the Fc domain fuses to the C-terminus of the extracellular stalk domain of the signal anchor domain. In one aspect, disclosed herein are engineered oncolytic viruses and/or fusion peptides, polypeptides, or proteins wherein the oncolytic virus and/or fusion peptides, polypeptides, or proteins that comprise one or more exogenous membrane bound immune cell targeting ligands and an uncleaved signal anchor, wherein the uncleaved signal anchor is neuraminidase, parainfluenza virus hemagglutinin-neuraminidase, transferrin receptor, MHC class II invariant chain, P glycoprotein, asialoglyoprotein receptor, or a neutral endopeptidase. For example, an engineered oncolytic virus can comprise a nucleotide sequence encoding a fusion protein comprising an immunoglobulin Fc domain (for example, an IgG1, IgG2, IgG3, and/or IgG4 Fc domain) and a neuraminidase signal anchor domain, wherein the Fc domain is modified to have an inverted orientation with the amino terminal end faced intracellularly as compared to the naturally occurring orientation of the Fc domain with respect to a cell. In other words, in the fusion peptides, polypeptides and proteins described herein in which the immune cell targeting ligand comprises an immunoglobulin Fc domain, the Fc domain is expressed on the extracellular side of the cell surface with its N-terminal side being attached to a membrane anchor peptide near the surface of cell membrane rather than the N-terminal side being at maximal distance from the cell surface. Alternatively, a fusion protein as described herein and encoded in an engineered oncolytic virus can comprise a NKG2D ligand (for example, RAET1, RAET1E, RAET1G, RAET1H, RAET1L, RAET1N, MICA, and/or MICB) and a neuraminidase signal anchor domain; or CD20 and a neuraminidase signal anchor domain; and/or CD19 and a neuraminidase signal anchor domain.

One embodiment of a fusion peptide, polypeptide, or protein comprising a membrane bound immune cell targeting ligand and an uncleaved signal anchor is set forth in SEQ ID NO: 1 MNPNQKITTIGSICLVVGLISLILQIGNIISI-WISHSIQTGSQNHTGICNRSDKTHTCPPCPAP ELLGGPSVFLFPPKPKDTLMISRTPE-VTCVVVDVSHEDPEVKFNWYVDGVEVHNAKTK PREEQYN-STYRVVSVLTVLHQDWLNGKEYKCKVSNKALPA-PIEKTISKAKGQPREPQV YTLPPSREEMTKNQVSLT-CLVKGFYPSDIAVEWESNGQPENNYKTTPPVLDSD GSFFLY SKLTVDKSRWQQGNVFSCSVMHEALHN-HYTQKSLSLSPGK and shown in FIG. 4.

As discussed herein there are numerous variants of the fusion peptides, polypeptides, and/or proteins; exogenous membrane bound immune cell targeting ligands, and/or signal anchor domains that are known and herein contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions
Original Residue Exemplary Conservative
Substitutions, others are known in the art.

| Original | Substitutions |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of a fusion protein. Specifically disclosed are variants of these and other proteins herein disclosed which have at least, 70% or 75% or 80% or 85% or 90% or 95%, 96%, 97%, 98%, or 99% sequence identity to the stated sequence. Those of skill in the art readily understand how to determine the sequence identity of two proteins. For example, the sequence identity can be calculated after aligning the two sequences so that the homology is at its highest level.

As this specification discusses various proteins and protein sequences it is understood that the nucleic acids that can encode those protein sequences, i.e., polynucleotides, are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. Accordingly, it is understood and herein contemplated that the person of skill in the art having possession of the amino acid sequence of the disclosed fusion peptides, polypeptides, or proteins, can envision and construct polynucleotides encoding said fusion peptides, polypeptides, and proteins. In one aspect, disclosed herein are polynucleotide sequence encoding the fusion proteins disclosed herein (for example, the fusion protein set forth in SEQ ID NO: 1).

In one aspect, it is contemplated herein that any NK cell activity induced by the engineered oncolytic cells and/or fusion peptides, polypeptides, or proteins disclosed herein can be increased by activating the NK cells through the contact of the NK cells with activating cytokines such as IL-2, IL-12, IL-18, IL-21 or IL-15. In one aspect, it is recognized that the activating cytokines can be expressed by the oncolytic viruses. Accordingly, in one aspect are engineered oncolytic viruses wherein the oncolytic virus expresses one or more exogenous membrane bound immune cell targeting ligands comprising an uncleaved signal anchor domain, wherein the oncolytic virus is further engineered to express one or more of IL-2, IL-12, 11-18, IL-21 or IL-15.

The oncolytic viruses disclosed herein can be constructed from any viral backbone. In one aspect, the virus is a modified or engineered Adenovirus, Adeno-associated virus, Herpesvirus (for example, Herpes Simplex virus-1, Herpes Simplex virus-2, Varicella-Zoster virus, Epstein-Barr virus, Cytomegalovirus, and/or Human Herpes virus-6), Poxvirus (for example, Variola virus, Vaccinia virus, Molluscum contagiosum virus, and/or Orf virus), Reovirus (for example, rotavirus), Picornavirus (for example, Enterovirus, Senecavirus, Poliovirus, Coxsackie virus, Rhinovirus, Hepatitis A virus, and/or foot-and-mouth disease virus), Togavirus (for example, Alphavirus, Semliki Forest virus, Eastern Equine Encephalitis virus, Sindbis virus, and/or Rubella virus), Coronavirus, Flavivirus (for example, Hepatitis C virus, Japanese Encephalitis virus, St. Louis Encephalitis virus, Murray Valley fever virus, Yellow Fever virus, West Nile virus, Zika virus, and/or Dengue virus), Filovirus (for example, Ebola virus and/or Marburg virus), Arenavirus (for example, Lassa fever virus, Lymphocytic choriomeningitis virus, Pichine virus, Junin virus, and/or Machupo virus), Bunyavirus (for example, Hantaan virus, and/or Rift Valley fever virus), Paramyxovirus (for example, human parainfluenza virus, mumps virus, simian virus 5, and/or measles virus), Rhabdovirus (for example, Vesicular stomatitis virus and/or rabies virus), Pneumovirus (for example, Respiratory syncytial virus,), Orthomyxovirus (for example, Influenza virus A, Influenza virus B, and/or Influenza C virus), Delta virus (for example Hepatitis D virus), Retrovirus (for example, Simian Immunodeficiency virus, Human Immunodeficiency virus type-1, and Human Immunodeficiency virus type-2, Rous sarcoma virus, Human T-cell Leukemia virus type-1 and/or Simian foamy virus), Hepadnavirus (for example Hepatitis B virus), Orthohepevirus (for example Hepatitis E virus), Human Papilomavirus, or Polyomavirus. For example, the oncolytic virus can be the HSV-1 oncolytic viruses HSV1716 or Talimogene laherparepvec, the modified adenovirus oncolytic virus H101, the poliovirus oncolytic virus PVSRIPO, the Reovirus oncolytic vbiurs reosylin, the seneca valley virus SVV-001, the coxsackie virus oncolytic virus Coxsackievirus A21, the enterovirus oncolytic virus Riga virus, or the vaccinia virus oncolytic viruses GL-ONC1 or JX-594. In one aspect, disclosed herein are modified or engineered oncolytic viruses wherein the oncolytic virus expresses an exogenous membrane bound immune cell targeting ligand comprising an uncleaved signal anchor domain; wherein the modified or engineered oncolytic virus is a parainfluenza virus, such as, for example a modified or engineered parainfluenza virus type 5 for example, a CPI parainfluenza, wild-type parainfluenza, or a CPI-WT parainfluenza chimeric virus encoding PN from CPI and the remainder of the viral backbone being WT parainfluenza).

In one aspect, it is recognized that facilitating the membrane fusion of the virus to a target cell such as a cancer cell can increase the rate and efficiency of delivery of genetic material from the oncolytic virus to the target cell. One method that fusion of the oncolytic virus to the target cell can be facilitated is through the use of fusogenic peptides, polypeptide, and proteins. Fusogenic peptides, polypeptides, and proteins, can include, but are not limited to viral fusogenic peptides, polypeptides, and proteins such as, for example, influenza hemagglutinin peptide (HA), Dengue fusogenic peptide, HIV envelope (Env), paramyxovirus (for example, parainfluenza virus and SV5) fusion protein (F) and paramyxovirus hemaglutinin-neuraminidase (HN). Accordingly, in one aspect, disclosed herein are oncolytic viruses comprising one or more exogenous membrane bound immune cell targeting ligand and an uncleaved signal anchor domain wherein the engineered oncolytic virus is a fusogenic oncolytic virus. In one aspect, the fusion peptide, polypeptide, or protein can be endogenous to the oncolytic virus or the virus can be engineered to express an exogenous fusion peptide, polypeptide, or protein. In other words, the oncolytic virus can either be native or engineered/modified to be fusogenic. For example, the backbone oncolytic virus can be a Reovirus, Poliovirus, or Adenovirus, which can be modified/engineered to comprise a fusogenic peptide, polypeptide, or protein and thus be fusogenic. Accordingly, in one aspect, disclosed herein are modified or engineered oncolytic viruses wherein the oncolytic virus expresses an exogenous membrane bound immune cell targeting ligand comprising an uncleaved signal anchor domain; wherein the modified or engineered oncolytic virus is a parainfluenza virus, such as, for example a modified or engineered parainfluenza virus type 5; and wherein the oncolytic virus expresses paramyxovirus F and/or HN. In one aspect, natively fusogenic oncolytic viruses can also be engineered to comprise further fusion peptides, polypeptides, or proteins. Such engineered fusogenic oncolytic viruses are hyperfusogenic. Thus, in one aspect, disclosed herein are fusogenic oncolytic viruses comprising a gene which codes for a peptide that allows a hyperfusogenic property that allows tumor cells to fuse.

As noted above, the disclosed fusion peptides, polypeptides, or proteins and/or modified oncolytic viruses are designed to maximize the number of immune cells (for example NK cells, T cells, CAR T cells, Innate lymphoid cells, Macrophages, and B cells (including plasma cells)) at the target cancer site and thus increase the immune cell activity (for example, NK cell activity, T cell activity, CAR T cell activity, and/or B cell activity (including plasma cell and antibody activity). Accordingly, in one aspect, disclosed herein are methods of targeting an immune cell to a cancer cell for cancer immunotherapy, the method comprising modifying an oncolytic virus by inserting the fusion peptides, polypeptides, or proteins; exogenous membrane bound immune cell targeting ligands, and/or signal anchor domains disclosed herein into the oncolytic viral genome and contacting the cell with the modified oncolytic virus.

1. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier. Thus, in one aspect, disclosed herein are pharmaceutical compositions comprising one or more engineered oncolytic viruses and a pharmaceutically acceptable carrier; wherein the oncolytic virus expresses an exogenous membrane bound immune cell targeting ligand selected from for example, an immunoglobulin Fc domain modified to have an inverted orientation with the amino terminal end faced intracellularly (for example, an IgG1, IgG2, IgG3, and/or IgG4 Fc domain); a NKG2D ligand (for example, RAET1, RAET1E, RAET1G, RAET1H, RAET1L, RAET1N, MICA, and/or MICB); and/or CD19) comprising an uncleaved signal anchor domain (for example, neuraminidase transmembrane segment).

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the type of oncolytic viral vector (i.e., the viral backbone of the oncolytic virus), the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. In one aspect, the oncolytic virus disclosed herein (or a composition comprising said virus) can be administered prior to the administration of any adoptively transferred NK cells. For example, the oncolytic virus can be administered 1, 2, 3, 4, 5, 6, 7, 8, 9, 10, 11, 12, 18 hours, 1, 2, 3, 4, 5, 6, 7, 8, 9, 10, 11, 12, 13, 14, 15, 20, 25, or 30 days prior to adoptive transfer of NK cells allowing the host immune system to respond to the oncolytic virus disclosed herein prior to NK cells being administered. In another aspect, the oncolytic virus and adoptively transferred NK cells can be administered concurrently to the same or different site, or simultaneously. In another aspect, the NK cells can be administered 1, 2, 3, 4, 5, 6, 7, 8, 9, 10, 11, 12, 18 hours, 1, 2, 3, 4, 5, 6, 7, 8, 9, 10, 11, 12, 13, 14, 21, 28, or 30 days prior to administration of the oncolytic virus disclosed herein or any compositions comprising said virus. When administered before or after the oncolytic virus, the NK cells can be administered to the same or a different site.

The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone can range from about 1 µg/kg to up to 100 mg/kg of body weight or more per day, depending on the factors mentioned above.

C. Methods of Treating Cancer

Oncolytic viruses have been shown in the art to be effective therapeutics for the treatment of cancer. The viruses lyse infected cancer cells at egress and the infection of cancer cells also stimulates the host immune response to kill the infected cells. It is understood and herein contemplated that the disclosed engineered viruses and/or fusion peptides, polypeptides, or proteins are similarly useful in the treatment of cancer and improve upon the efficacy of such oncolytic viruses to recruit NK cells to infected cancer cells. Thus, in one aspect, the disclosed oncolytic viruses expressing one or more peptides, polypeptides, or proteins comprising a membrane bound immune cell targeting ligand (for example, an immunoglobulin Fc domain (for example, an IgG1, IgG2, IgG3, and/or IgG4 Fc domain comprising an inverted orientation with the amino terminal end faced intracellularly); a NKG2D ligand (for example, RAET1, RAET1E, RAET1G, RAET1H, RAET1L, RAET1N, MICA, and/or MICB); and/or a CD19) and an uncleaved signal anchor domain and/or fusion peptides, polypeptides, or proteins comprising a membrane bound immune cell targeting ligand and an uncleaved signal anchor domain can be used to treat cancer. In one aspect, the engineered oncolytic virus can be modified to comprise the fusion peptide, polypeptide, or protein. Where the one or more exogenous membrane bound immune cell targeting ligands is an immunoglobulin Fc domain, it is understood that the Fc domain can be modified to be expressed on the extracellular side of the cell surface with its N-terminal side being attached to a membrane anchor peptide near the surface of cell membrane.

A non-limiting list of different types of cancers that can be treated by administering to a subject one of the oncolytic viruses disclosed herein is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general. A representative but non-limiting list of cancers that the disclosed oncolytic viruses and compositions comprising the same can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, merkel cell carcinoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Accordingly, in one aspect, disclosed herein are methods of treating a cancer comprising administering to a subject a composition comprising one or more engineered oncolytic viruses and/or fusion peptides, polypeptides, or proteins (including oncolytic viruses expressing the disclosed fusion peptides, polypeptides, or proteins), wherein the one or more oncolytic virus expresses one or more fusion peptides, polypeptides, or proteins comprising an exogenous a membrane bound immune cell targeting ligand. In one aspect, a fusion peptide, polypeptide or protein as disclosed herein, which comprises an exogenous a membrane bound immune cell targeting ligand, includes an uncleaved signal anchor domain comprising: a cytoplasmic tail region, a transmembrane region and an extracellular stalk region; and an immune cell targeting ligand comprising an N-terminus fused to a C-terminus of the extracellular stalk region. Thus the fusion peptide, polypeptide or protein provides a membrane bound immune cell targeting ligand is (such as, for example, immunoglobulin Fc domain (for example, an IgG1, IgG2, IgG3, and/or IgG4 Fc domain) modified to have an inverted orientation with respect to a cell, with the amino terminal end faced intracellularly rather than extracellularly, as compared to the naturally occurring orientation of the ligand, a NKG2D ligand (for example, RAET1, RAET1E, RAET1G, RAET1H, RAET1L, RAET1N, MICA, and/or MICB); and/or another targetable ligand (for example, CD19 or CD20)).

It is understood and herein contemplated that the methods of treatment employ oncolytic viruses which have been modified and/or fusion peptides, polypeptides, or proteins that have been synthesized to increase NK cell activity against target cancer cells. Thus, the therapeutic activity of the oncolytic viruses and/or fusion peptides, polypeptides, or proteins disclosed herein can be augmented through the adoptive transfer of immune cells (such as, for example, Natural Killer (NK) cells, including, but not limited to genetically modified NK cells) or any combination thereof into the subject during oncolytic viral therapy with any of the oncolytic viruses disclosed herein. Accordingly, in one aspect, disclosed herein are methods of treating cancer further comprising adoptively transferring immune cells, such as, for example NK cells (including, for example, genetically modified NK cells) and/or CD19 targeting anti-CD19 CAR T cells to the subject. In one aspect, the NK cells can be modified to express CD19 targeting anti-CD19 chimeric antigen receptors.

In one aspect, it is understood and herein contemplated that some targeting ligands used in the disclosed oncolytic viruses are not a direct ligand for a receptor on an NK cell. In one aspect, disclosed herein are methods of treating cancer comprising administering to the subject an oncolytic virus comprising one or more membrane bound immune cell targeting ligands comprising an uncleaved signal anchor domain, said method further comprising administering to the subject one or more antibodies that recognize the targeting ligand (for example, anti-CD19 antibodies (for example, MDX1342, MEDI-551, AFM11, XmAb 5871, MOR-208, SGN-19A, SAR3419, Blinatumomab, or taplitumomab) or anti-CD-20 antibodies (for example, rituximab, ofatumumab, obinutuzumab, veltuzumab, or ocrelizumab). It is understood that the disclosed methods of treating cancer comprising administering to the subject an oncolytic virus comprising one or more membrane bound immune cell targeting ligands comprising an uncleaved signal anchor domain and an antibody that recognizes a target ligand, said method can further comprise the administration of any of the immune cells disclosed above. Additionally, the disclosed methods can further comprise the administration of any anti-cancer therapeutic known to those of skill in the art.

In the disclosed cancer treatment methods, it can be desirable to achieve a degree of NK cell activation and/or expansion that reaches an effective therapeutic dose. NK cells proliferate in an in vitro culture exponentially and preferentially within a mixture of peripheral blood mononuclear cells (PBMC) when stimulated cytokines (such as IL-15 or IL-21) and ligands for activating receptors (such as 4-1BBL) expressed on the surface of stimulator cells. Stimulation with membrane bound IL-21 was found to stimulate continuous propagation of NK cells over countless generations allowing for continuous expansion of NK cells provided that the culture is periodically replenished with fresh stimulatory cells. While these methods allow for efficient in vitro NK cell expansion, the need for live feeder cells makes the methodology difficult to transfer to clinical settings that do not have large GMP facility and capability. Also, NK cells that are infused into the patient may stop dividing due to the lack of continued stimulation by the feeders. Through the use of plasma membrane (PM) particles, exosomes (EX), or feeder cells comprising one or more activating agents, stimulatory peptides, cytokines, and/or adhesion molecules to contact and activate and/or expand NK cells these hurdles are overcome. Examples of NK cell activating agents and stimulatory peptides include, but are not limited to, 41BBL, IL-2, IL-12, IL-21, IL-18, MICA, LFA-1, 2B4, BCM/SLAMF2, CCR7 and/or other homing receptors. Examples of cytokines include, but are not limited to, IL-2, IL-12, IL-21, and IL-18. Examples of adhesion molecules include, but are not limited to LFA-1, MICA, BCM/SLAMF2. For example, feeder cells or a plasma membrane particle (PM particle) or exosomes (EX) are prepared from feeder cells expressing membrane bound IL-21 (FC21 feeder cells, PM21 particles, and EX21 exosomes, respectively). The membrane bound IL21 expressing FC21 cells, PM21 particles, and EX21 exosomes can further comprise additional one or more activating agents, stimulatory peptides, cytokines, and/or adhesion molecules including, but not limited to 41BBL, IL-2, IL-12, IL-18, MICA, LFA-1, 2B4, BCM/SLAMF2, CCR7 (for example, PM21 particle, EX21 exosome, or FC21 feeder cell expressing 41BBL and membrane bound interleukin 21). Accordingly, in one aspect, disclosed herein are methods of treating a cancer comprising administering to a subject a composition comprising one or more engineered oncolytic viruses wherein the one or more oncolytic viruses express one or more exogenous membrane bound immune cell targeting ligand (for example, an immunoglobulin Fc domain (for example, an IgG1, IgG2, IgG3, and/or IgG4 Fc domain) modified to have an inverted orientation with respect to a cell, with the amino terminal end faced intracellularly rather than extracellularly, as compared to the naturally occurring orientation of the ligand, a NKG2D ligand (for example, RAET1, RAET1E, RAET1G, RAET1H, RAET1L, RAET1N, MICA, and/or MICB); and/or CD19) comprising an uncleaved signal anchor domain; further comprising adoptively transferring to the subject immune cells, such as, for example NK cells (such as, for example, genetically modified NK cells) or CD19 targeting anti-CD19 CART cells to the subject, wherein the immune cells are NK cells, the NK cells are stimulated and expanded with one or more NK cell stimulating agents such as a cytokine (such as, for example, IL-12; IL-15; IL-18; and any combination thereof including IL-12 and IL-15; IL-12 and IL-18; IL-15 and IL-18; and IL-12, IL-15, and IL18), growth factor, synthetic ligand, NK cell stimulating particles, NK cell stimulating exosomes, and/or NK cell stimulating feeder cells including NK cell stimulating particles, exosomes, and/or feeder cells comprising IL-21, 4-1BBL, IL-21 and 4-1BBL; or any combination of cytokines or NK cell stimulating particles, exosomes, or feeder cells thereof.

In one aspect, the plasma membrane particle or exosome can be purified from NK cell feeder cells. NK cell feeder cells for use in the claimed invention and for use in making the plasma membrane particles and exosomes disclosed herein can be either irradiated autologous or allogeneic peripheral blood mononuclear cells (PBMCs) or nonirradiated autologous or allogeneic PBMCs, RPMI8866, HFWT, K562, K562 cells transfected with membrane bound IL-15 and 41BBL, K562 cells transfected with membrane bound IL-21 and 41BBL, or EBV-LCL. In some aspects, the NK cell feeder cells can be K562 cells transfected with membrane bound IL-21 and 41BBL or K562 cells transfected with membrane bound IL-15 and 41BBL.

D. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 1:
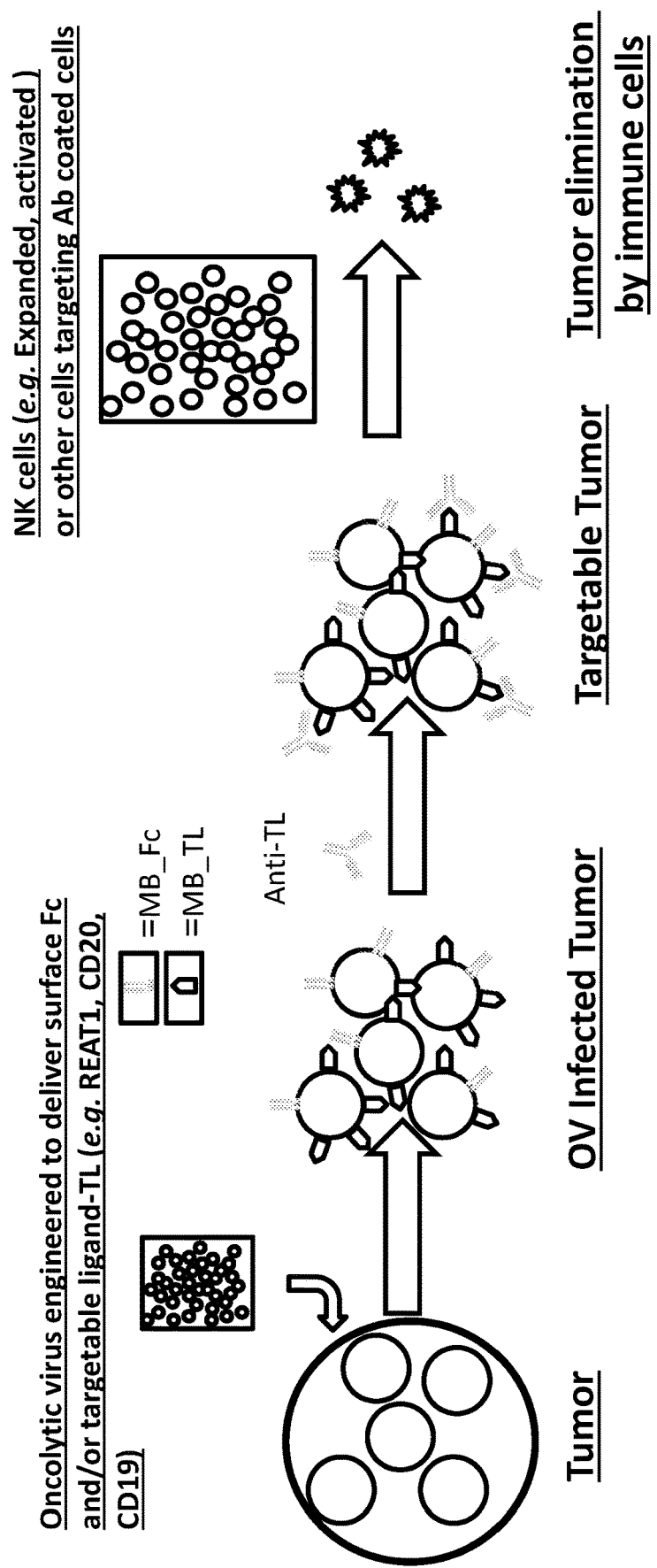
Figure 3A:
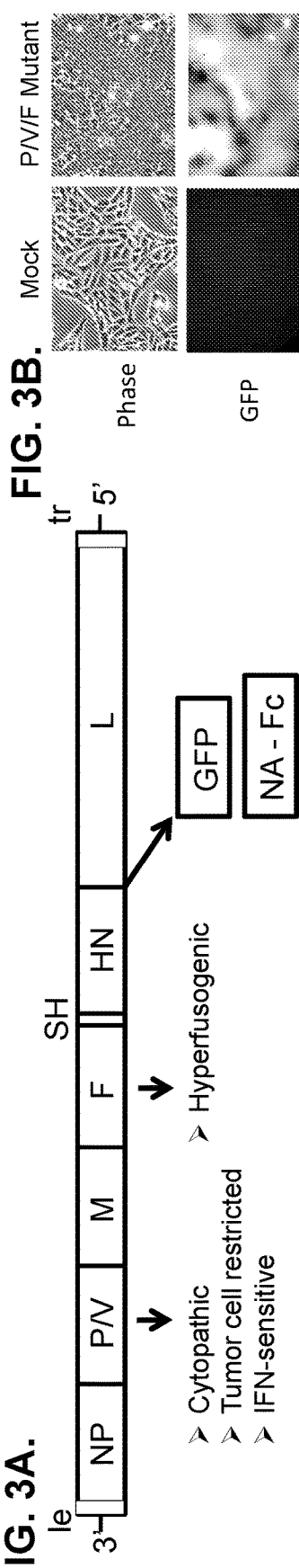
FIG. 3A shows a schematic of the genes in an engineered oncolytic virus including insertion points for a membrane bound immune cell targeting ligand and site of any fusogenic mutations.
Figure 3B:
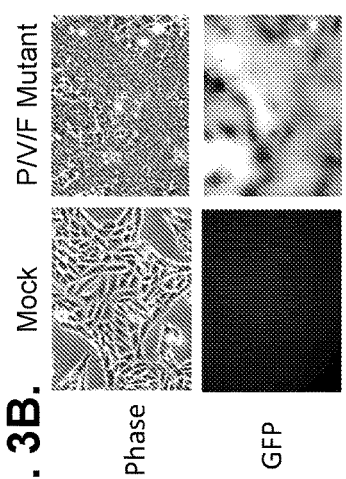
FIG. 3B shows a micrograph of Vero cells following infection with the oncolytic virus.
Figure 3D:
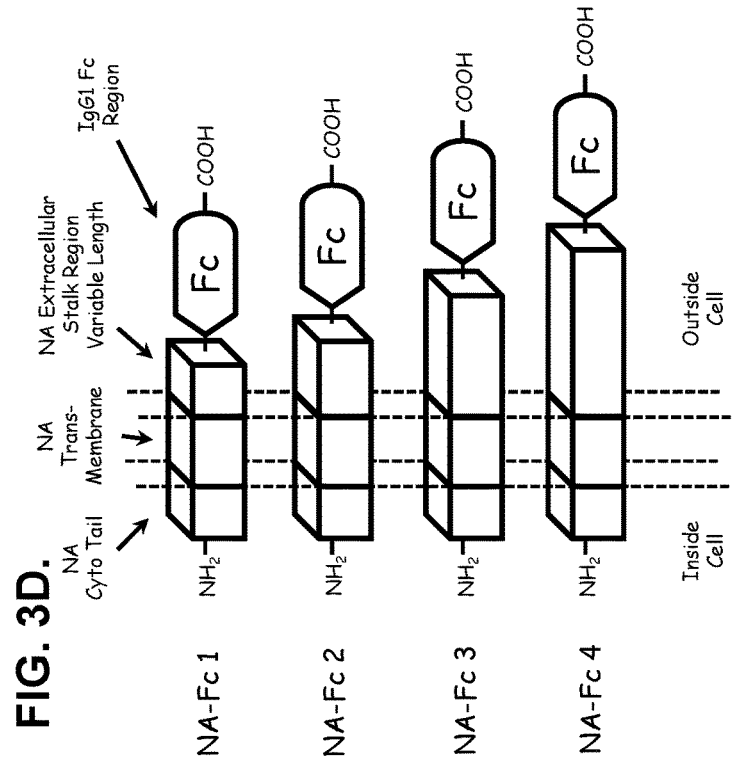
FIG. 3D shows alternative constructions of membrane bound immune cell targeting ligands comprising an Fc domain comprising a neuraminidase signal anchor and increasing neuraminidase stalk lengths.
Figure 3C:
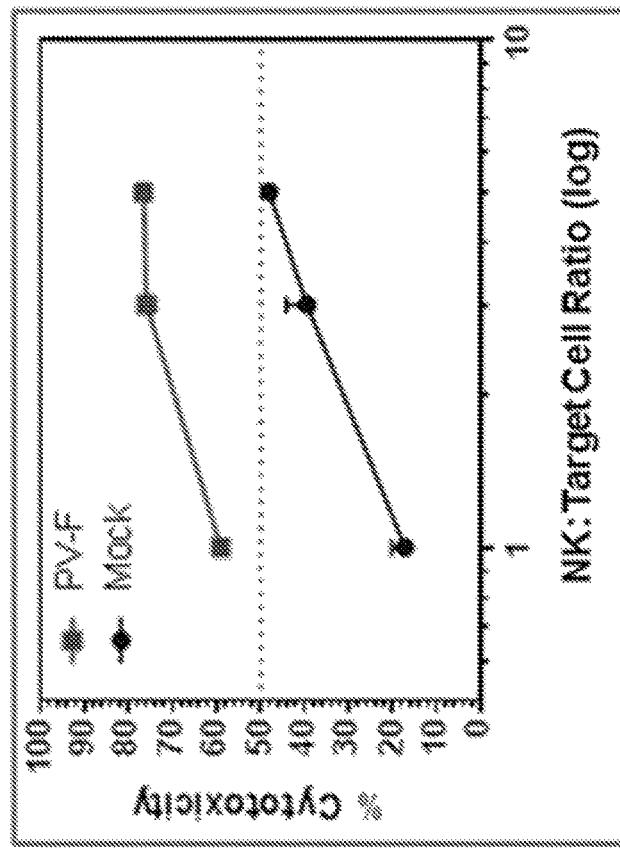
FIG. 3C shows that PM21 activated NK cells recognize and kill tumor cells more effectively when treated the engineered oncolytic viruses as compared to mock treated tumor targets.
Figure 4:
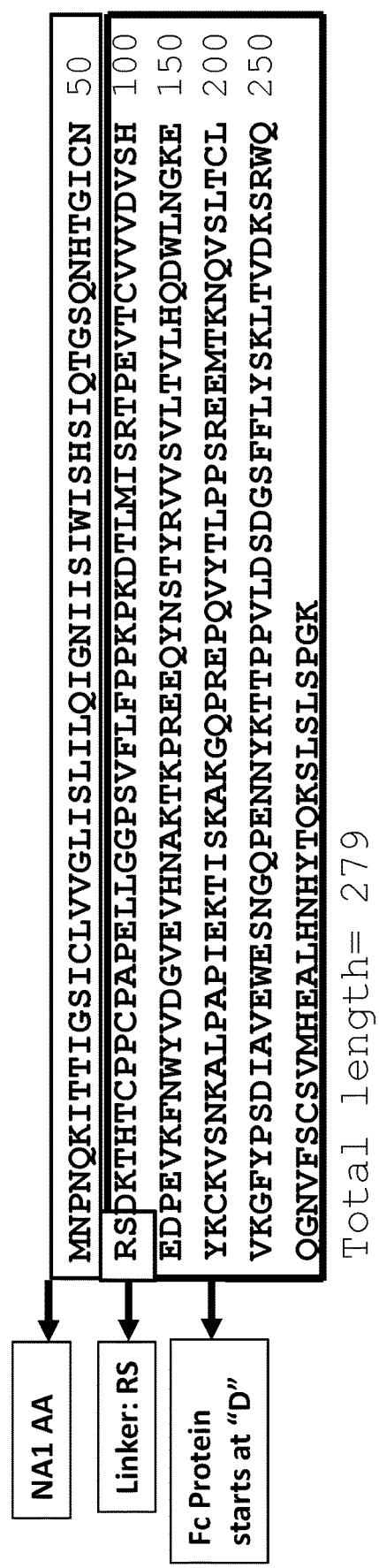
FIG. 4 shows an example of a membrane bound immune cell targeting ligand sequence. Here neuraminidase signal anchor is fused to an IgG Fc domain by an RS linker (i.e., a restriction site linker)(SEQ ID NO: 1).
Figure 5:
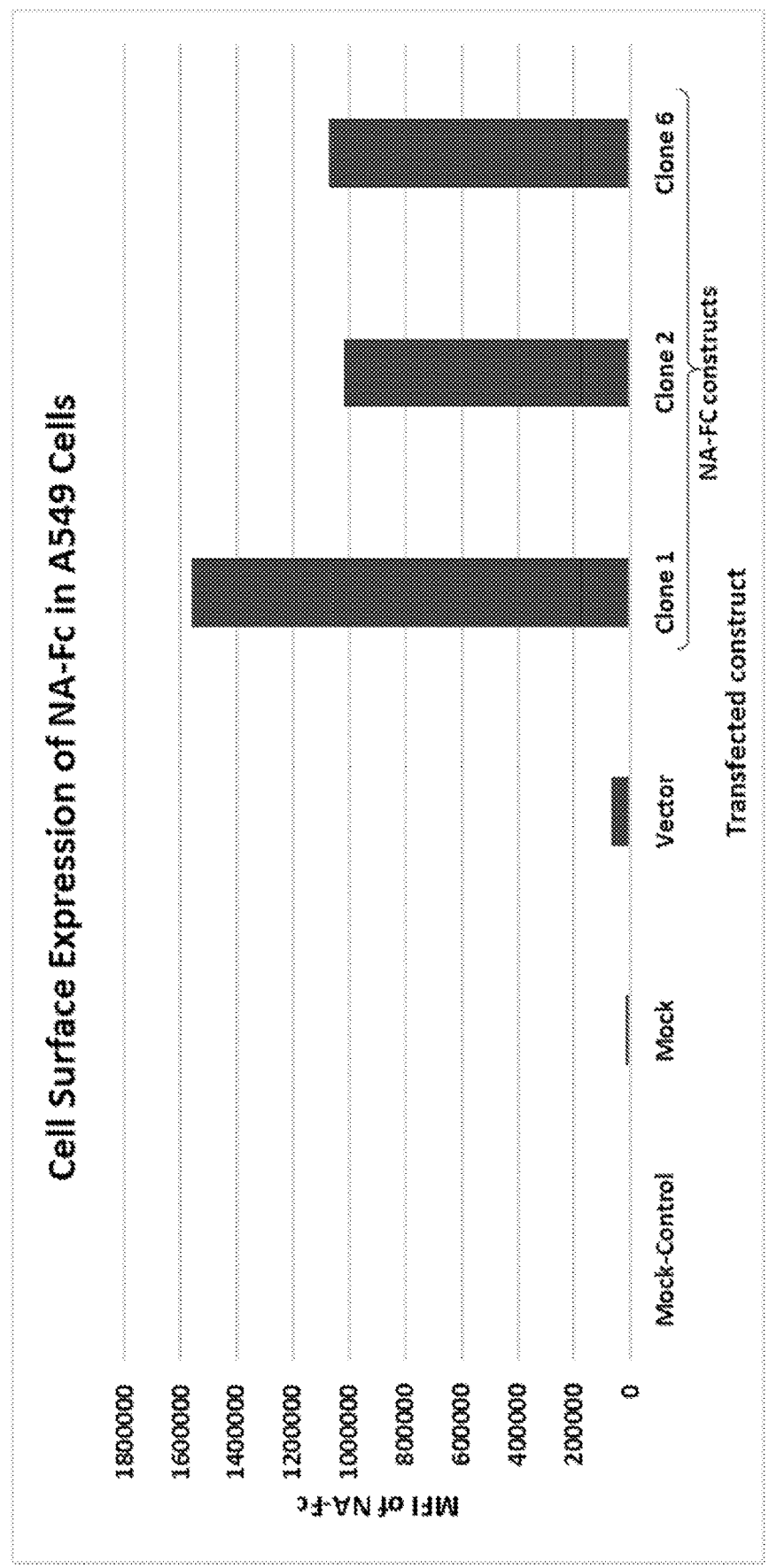
FIG. 5 shows the flow cytometry analysis for ability of the NA-Fc fused construct to correctly express the membrane bound Fc targeting ligand on the surface of infected cells when transfected by plasmid carrying the NA-Fc construct.

Herein, the oncolytic virus is further improved for enhanced immune stimulation and used to deliver immune targetable ligand, specifically an exogenous membrane bound immune cell targeting ligand such as, for example, a membrane bound Fc domain (MB Fc) of an antibody, for enhanced efficacy of adoptively transferred NK cells (FIG. 1). The Fc domain of an antibody is recognized by the CD16 (FcγIII receptor) on NK cells which then elicits antibody-dependent cell cytotoxicity (ADCC). NK cells killing of target cells via ADCC is less susceptible to immune suppression mechanisms deployed by tumors, thus marking the tumor surface with antibody derived Fc's results in more effective killing via ADCC for efficient tumor elimination. To construct membrane bound immune cell targeting ligand, the uncleaved signal anchor from a Type II integral membrane protein can be fused to a targeting ligand. Effectively, the globular head typically present on a Type II integral membrane protein is replaced with the targeting ligand (FIG. 2).

Artificial Fc-containing proteins can be delivered to tumor using tumor-targeting oncolytic virus to "mark" cancer cells for ADCC in the absence of targetable antigen or therapeutic antibody. The chimeric protein can mimic a surface-bound antibody: type II membrane orientation fused to a with a C-terminally extracellularly exposed Fc domain that is in inverted orientation relative to the naturally occurring orientation of the ligand, such that the amino terminal end of the Fc domain faces the cell membrane (i.e, intracellularly) in monomeric, dimeric or multimeric form. Alternatively, other targetable ligands (e.g. CD19, RAET1, RAET1E, RAET1G, RAET1H, RAET1L, RAET1N, MICA, MICB, and/or CD20) can be delivered via oncolytic virus directly the surface membrane where the targeting ligand (such as RAET1, RAET1E, RAET1G, RAET1H, RAET1L, RAET1N, MICA, and/or MICB) can be recognized directly by the NKG2D receptor on NK cells or along with therapeutic antibody against the targetable ligand (e.g., CD20 or CD19) capable of engaging ADCC (e.g. anti-CD20-Rittman, ofatumumab, obtinutuzumab, veltuzumab, Ocrelizumab etc. or anti-CD19 MDX1342, MEDI-551, AFM11, XmAb 5871, MOR-208, SGN-19A, SAR3419, Blinatumomab, or taplitumomab etc.) and/or along with CART cells that target the targeting ligand (e.g., anti-CD19 CART cells). An example of a suitable enabling oncolytic virus for delivery of the membrane bound (MB Fc) or membrane bound (MB_TL) is P/V/F mutant of Parainfluenza virus 5. This engineered P/V/F mutant has mutations in: 1) the P/V gene, which encodes proteins involved in both polymerase functions (P) and inhibition of immune responses (V) (FIG. 3A), and 2) the viral F gene, which encodes the fusion protein involved in virus entry and generation of syncytia (FIG. 3B). The P/V mutations restricted the virus for growth in tumor cells, and the virus induces cell death and antiviral responses (14-16). The F mutation results in a virus that generates massive cell-cell fusion (syncytia), a desirable property that spreads the virus through a tumor and kills through necrosis. This is evident in the micrograph in FIG. 3B, which shows massive syncytia in Vero cells following P/V/F infection. P/V/F infected cancer cells are also recognized and killed more efficiently by human PM21-NK cells (FIG. 3C). In this experiment, human ovarian SKOV3-Luc cells were mock infected or infected at an MOI=10 with the P/V/F virus and 20 h later incubated at various ratios with human NK cells, produced by a PM21-particle approach. The percentage of viable cells was determined after 24 h at a time when P/V/F cytopathic effect in the absence of NK cells was not evident (cell viability >90%). As shown in FIG. 3C, PM21-NK cells were much more effective at killing PV/F infected cells as compared to mock infected, where at least 5 times less NK cells were needed to kill 50% of target cells. Thus, P/V/F is a suitable enabling virus to use for the intended use with adoptive NK cell treatment. As a delivery vector this virus also has a number of strong enabling properties, including: (1) small genome with no known packaging constraints to add multiple foreign genes; (2) efficient infection of non-dividing cells enabling production at high titers (>$10^{10}$ pfu/ml); (3) cytoplasmic replication without integration into host DNA and with no observed recombination; (4) infects humans but infection is not associated with disease or pathogenic characteristics. To get the Fc domain on the plasma membrane, membrane targeting domain from the well characterized influenza virus neuraminidase protein (NA) can be used which consists of the N-terminal cytoplasmic tail, an uncleaved signal-anchor which serves as a transmembrane domain, and a stalk region which extends from the plasma membrane. As shown in FIG. 3D construct composes of NA-Fc chimeras where the Fc domain is linked to increasing lengths of the NA stalk region. The NA-Fc can be inserted into recombinant P/V/F virus to generate a novel oncolytic virus (FIG. 3A) which is specific for tumor versus normal cells (due to PN mutations) and can enhance ADCC by NK cells (A). An example of the amino acid sequence of one of the NA-Fc constructs is shown on FIG. 4 its ability to present Fc on the surface of transfected tumor cells on FIG. 5. In this experiment A549 lung cancer cells were transfected with mock control, empty vector or vector encoding the NA1 Fc and then stained for surface expression the next day with anti-human Fc antibody (APC anti-human IgG Fc HP6017-Biolegend) to detect presence of Fc on the cell surface. Only cells transected with NA1_Fc had high mean fluorescence intensity in the APC channel reflective of anti-Fc antibody bound to the surface of Fc expressing cells. Thus, NA is suitable membrane anchor to express Fc in the proper orientation. Other examples of suitable transmembrane domains with an $NH_2$—terminal cytoplasmic domain and COOH-terminal ectodomain ($N_{cyt}$ topology) include but are not limited to the transferrin receptor, asiagoglycoprotein, the family of Golgi-resident glycosyltransferases and the paramyxovirus HN protein.

Two NK cell resistant cell lines-A549 non-small lung carcinoma and SKOV-3 ovarian cancer cell line were used to collect poof-of-concept studies to show that oncolytic virus can sensitize tumor target to NK cell killing (FIGS. 6, 8, 11) and thus can be also used as a delivery vehicle to deliver "universal targetable ligands" to tumor cells. Many viruses including P/V/F are known to be able to deliver DNA to the infected cells and lead to expression of virally encoded proteins in the host cell. Fc domain of antibodies that engages CD16 receptor on NK cells is one example of above mentioned "universal targetable ligand". The attachment of the Fc domain to the neuramidase (NA) stalk allows expression of the Fc on the cell surface (FIGS. 7 and 9). As expected, stable expression of NA1-Fc on either SKOV-3 cells or A549 cells led to increased killing by NK cells and this effect was additive with P/V/F infection (FIGS. 3 and 6). Furthermore by increasing the length of the neuramidase stalk domain the killing via the Fc recognition was further enhanced (FIG. 10). Thus, combine of the use of OVs to enhance killing as well as to deliver "universal ligands' can sensitize even the most NK cell resistant cancer cell lines into NK cell sensitive.

What is claimed is:

1. An engineered oncolytic virus wherein the oncolytic virus expresses one or more exogenous membrane bound immune cell targeting ligands comprising an uncleaved signal anchor, wherein the one or more exogenous membrane bound immune cell targeting ligands comprise an immunoglobulin Fc domain modified to have an inverted orientation with its amino terminal end facing intracellularly.

2. The engineered oncolytic virus of claim 1, wherein the engineered oncolytic virus is a fusogenic oncolytic virus.

3. The engineered oncolytic virus of claim 1, wherein the uncleaved signal anchor is a neuraminidase transmembrane segment.

4. A pharmaceutical composition comprising the engineered oncolytic virus of claim 1 and a pharmaceutically acceptable carrier.

5. A method for treatment of cancer, comprising administering to a subject the engineered oncolytic virus of claim 1.

6. The method of claim 5, further comprising adoptively transferring to the subject natural killer (NK) cells, antibodies that target one or more of the one or more exogenous membrane bound immune cell targeting ligands, or CAR T cells that are designed to target one or more of the one or more exogenous membrane bound immune cell targeting ligands.

7. A method of treating cancer, comprising administering to a subject the engineered oncolytic virus of claim 1.

8. The method of claim 7, wherein the method further comprises adoptively transferring natural killer (NK) cells, engineered CD19 targeting anti-CD19 CAR-T cells, CD20 targeting anti-CD20 CAR-T cells, B cells one or more of the exogenous membrane bound immune cell targeting ligands or plasma cells that secrete antibodies specific for one or more of the exogenous membrane bound immune cell targeting ligands.

9. The method of claim 8, wherein the NK cells are stimulated and expanded with one or more NK cell stimulating agents; wherein the one or more NK cell stimulating agent is a cytokine, growth factor, synthetic ligand, NK cell stimulating particle, NK cell stimulating exosome, or NK cell stimulating feeder cell.

10. The method of claim 9, wherein the one or more NK stimulating agent is an NK cell stimulating particle, NK cell stimulating exosome, or NK cell stimulating feeder cell; and wherein the one or more agents comprise IL-21, 4-1BBL or a fragment thereof.

11. The method of claim 9, wherein the one or more NK cell stimulating agents comprise at least one cytokine selected from the group consisting of IL-2, IL-12, IL-18, IL-15 or a combination thereof.

12. The method of claim 8, wherein the NK cells are engineered to express CD19 targeting anti-CD19 chimeric antigen receptors or CD20 targeting anti-CD20 chimeric antigen receptors.

13. The method of claim 7, wherein the cancer is selected from the group consisting of leukemia, lymphoma, myeloma, melanoma, colorectal cancer, breast cancer, ovarian cancer, renal cell cancer, malignant melanoma, malignant glioma, neuroblastoma, non small cell lung carcinoma renal cell carcinoma, merkel cell carcinoma, skin cancer, brain cancer, pancreatic adenocarcinoma, malignant mesothelioma, lung adenocarcinoma, lung small cell carcinoma, lung squamous cell carcinoma, anaplastic thyroid cancer or head and neck squamous cell carcinoma.

14. A fusion protein comprising an uncleaved signal anchor domain comprising: a cytoplasmic tail region, a transmembrane region and an extracellular stalk region; and an immunoglobulin Fc domain modified to have an inverted orientation with its amino terminal end facing intracellularly and wherein the amino terminal end of the immunoglobulin Fc domain is fused to a C-terminus of the extracellular stalk region.

15. The fusion protein of claim 14, wherein the Fc domain further comprises at least one amino acid modification selected from the group consisting of: 256A/K290A/S298A/E333A/K334A or L235V/F243L/R292P/Y300L/P396L.

16. The fusion protein of claim 14, wherein the uncleaved signal anchor domain comprises a signal anchor domain selected from the signal anchor domain of neuraminidase, parainfluenza virus hemagglutinin-neuraminidase, transferrin receptor, MHC class II invariant chain, P glycoprotein, asialoglycoprotein receptor, and a neutral endopeptidase.

17. The fusion protein of claim 14, comprising an amino acid sequence having at least 95% sequence identity to the amino acid sequence of SEQ ID NO: 1.

18. A polynucleotide sequence encoding the fusion protein of claim 17.

19. A host virus comprising a modified viral genome comprising the polynucleotide of claim 17.

20. The host virus of claim 19, wherein the host virus is an oncolytic virus.

21. The host virus of claim 20, wherein the host virus is a cell fusogenic oncolytic virus.

22. A method of targeting an immune cell to a cancer cell for cancer immunotherapy, the method comprising obtaining a modified oncolytic virus comprising the polynucleotide of claim 18 and contacting the cell with the modified oncolytic virus.

23. The engineered oncolytic virus of claim 1, wherein the uncleaved signal anchor is a neuraminidase transmembrane segment.

24. The engineered oncolytic virus of claim 23, wherein the engineered immunoglobulin Fc domain modified to have an inverted orientation with the amino terminal end facing intracellularly is fused to the neuraminidase transmembrane segment by a peptide linker of 2-20 amino acids in length.

25. The engineered oncolytic virus of claim 24, wherein the peptide linker is a restriction site linker.

26. The engineered oncolytic virus of claim 1, wherein the engineered immunoglobulin Fc domain comprises an amino acid modification wherein the N-terminus of the Fc domain fuses to the C-terminus of an extracellular stalk region of the uncleaved signal anchor domain.

27. The engineered oncolytic virus of claim 26, wherein the immunoglobulin Fc domain further comprises at least one amino acid modification selected from the group consisting of: 256A/K290A/S298A/E333A/K334A or L235V/F243L/R292P/Y300L/P396L.

* * * * *

SEQUENCE LISTING

```
<160> NUMBER OF SEQ ID NOS: 1

<210> SEQ ID NO 1
<211> LENGTH: 279
<212> TYPE: PRT
<213> ORGANISM: Artificial Sequence
<220> FEATURE:
<223> OTHER INFORMATION: Synthetic constructs

<400> SEQUENCE: 1

Met Asn Pro Asn Gln Lys Ile Thr Thr Ile Gly Ser Ile Cys Leu Val
1               5                   10                  15

Val Gly Leu Ile Ser Leu Ile Leu Gln Ile Gly Asn Ile Ile Ser Ile
                20                  25                  30

Trp Ile Ser His Ser Ile Gln Thr Gly Ser Gln Asn His Thr Gly Ile
            35                  40                  45

Cys Asn Arg Ser Asp Lys Thr His Thr Cys Pro Pro Cys Pro Ala Pro
        50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Gln Val Lys Phe Asn Trp Tyr Val Asp
            100                 105                 110

Gly Val Glu Val His Asn Ala Lys Thr Lys Pro Arg Glu Glu Gln Tyr
        115                 120                 125

Asn Ser Thr Tyr Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Ala Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Asn Gly Gln Pro Glu Asn Asn Tyr Lys
    210                 215                 220

Thr Thr Pro Pro Val Leu Asp Ser Asp Gly Ser Phe Phe Leu Tyr Ser
225                 230                 235                 240

Lys Leu Thr Val Asp Lys Ser Arg Trp Gln Gln Gly Asn Val Phe Ser
                245                 250                 255

Cys Ser Val Met His Glu Ala Leu His Asn His Tyr Thr Gln Lys Ser
            260                 265                 270

Leu Ser Leu Ser Pro Gly Lys
        275
```